(12) United States Patent
Tunquist et al.

(10) Patent No.: US 9,561,214 B2
(45) Date of Patent: Feb. 7, 2017

(54) METHOD OF TREATMENT USING INHIBITORS OF MITOSIS

(75) Inventors: Brian J. Tunquist, Broomfield, CO (US); Duncan H. Walker, Boulder, CO (US); Richard D. Woessner, Broomfield, CO (US)

(73) Assignee: Array BioPharma Inc., Boulder, CO (US)

( * ) Notice: Subject to any disclaimer, the term of this patent is extended or adjusted under 35 U.S.C. 154(b) by 885 days.

(21) Appl. No.: 12/581,072

(22) Filed: Oct. 16, 2009

(65) Prior Publication Data

US 2010/0099697 A1  Apr. 22, 2010

Related U.S. Application Data

(60) Provisional application No. 61/106,079, filed on Oct. 16, 2008.

(51) Int. Cl.
*A61K 31/433* (2006.01)
*A61K 31/00* (2006.01)

(52) U.S. Cl.
CPC ............ *A61K 31/433* (2013.01); *A61K 31/00* (2013.01)

(58) Field of Classification Search
None
See application file for complete search history.

(56) References Cited

U.S. PATENT DOCUMENTS

| | | | |
|---|---|---|---|
| 4,046,910 A | 9/1977 | Johnson | |
| 6,346,524 B1 | 2/2002 | Ragab | |
| 6,838,467 B2 | 1/2005 | End | |
| 7,449,486 B2 | 11/2008 | Hans et al. | |
| 7,795,282 B2 | 9/2010 | Hans et al. | |
| 7,956,073 B2 | 6/2011 | Hans et al. | |
| 8,268,871 B2 | 9/2012 | Hans et al. | |
| 8,324,257 B2 | 12/2012 | Ahrendt et al. | |
| 8,580,828 B2 | 11/2013 | Hans et al. | |
| 8,623,895 B2 | 1/2014 | Hans et al. | |
| 9,102,639 B2 | 8/2015 | Hans et al. | |
| 2005/0063949 A1 | 3/2005 | Visor | |
| 2005/0136055 A1 | 6/2005 | Gladue et al. | |
| 2005/0182028 A1 | 8/2005 | Chen | |
| 2005/0267166 A1 | 12/2005 | Gordon et al. | |
| 2006/0089391 A1 | 4/2006 | Gordon et al. | |
| 2006/0100161 A1* | 5/2006 | Hans et al. ................ 514/19 |
| 2007/0112044 A1 | 5/2007 | Murakata et al. | |
| 2007/0219268 A1 | 9/2007 | Hausheer | |
| 2008/0090896 A1 | 4/2008 | Brookler | |
| 2008/0153887 A1 | 6/2008 | Cox et al. | |
| 2010/0041719 A1 | 2/2010 | Ahrendt et al. | |
| 2010/0331283 A1 | 12/2010 | Hans et al. | |
| 2011/0201651 A1 | 8/2011 | Hans et al. | |
| 2014/0018399 A1 | 1/2014 | Hans et al. | |
| 2015/0191490 A1 | 7/2015 | Hans et al. | |
| 2015/0210658 A1 | 7/2015 | Hans et al. | |

FOREIGN PATENT DOCUMENTS

| | | |
|---|---|---|
| JP | 2005232016 A | 9/2005 |
| WO | 03/079973 A2 | 10/2003 |
| WO | 2006/031348 A2 | 3/2006 |
| WO | 2006/031607 A2 | 3/2006 |
| WO | 2007/136636 A1 | 11/2007 |

OTHER PUBLICATIONS

O'Connor et al. (Journal of Clinical Oncology, 26 (15S), May 2008:8539).*
Blagden et al. (British Journal of Cancer, 98:894-899, Mar. 2008).*
Heath et al. ( Journal of Clinical Oncology, 2006 ASCO Annual Meeting Proceedings Part I. vol. 24, No. 18S (Jun. 20 Supplement), 2006: 2026).*
Sausville et al. (Cancer Research, 2006, vol. 66, pp. 3351-3354).*
Johnson et al. (British J. of Cancer, 2001, 84(10):1424-1431).*
Askari et al. "Thiadiazoles and Thiadiazolines. Part 1. Reaction of Thiourea and Ethylenethiourea with Chlorodiazabutadienes: a New Route to 4-Amidino-1,3,4-thiadiazolines", J.C.S. Perkin I, (1981), pp. 360-365.
Chan, et al., "Characterization of the Kinetochore Binding Domain of CENP-E Reveals Interactions with the Kinetochore Proteins CENP-F and hBUBR1." J. Cell Biology. vol. 143, No. 1 (Oct. 5, 1998): pp. 49-63.
Denduluri, et al., "Phase II trial of ixabepilone, an epothilones B analog, given daily for three days every three weeks, in metastatic breast cancer." Invest. New Drugs. 25 (Aug. 25, 2006): pp. 63-67.
Gautschi, et al., "Aurora Kinases as Anticancer Drug Targets." Clin. Cancer Res. 14(6) (Mar. 15, 2008): pp. 1639-1648.

(Continued)

*Primary Examiner* — Bong-Sook Baek
(74) *Attorney, Agent, or Firm* — Viksnins Harris & Padys PLLP; Corey M. Williams

(57) ABSTRACT

Methods of treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 24 to 48 hours after the first dose.

3 Claims, 19 Drawing Sheets

(56) References Cited

OTHER PUBLICATIONS

Hammond, et al., "Phase (Ph) I evaluation of the dolastatin analogue synthadotin (SYN-D; ILX651): Pooled data analysis of three alternate schedules in patients (pts) with advanced solid tumors." J. Clin. Oncology. 2004 Suppl. Abstract 3068 14s (2004).
Moss et al., "Thiadiazoles and Thiadiazolines. Part 3.(1) Synthesis of Triazol-3-yl-Δ2-1,3,4-thiadiazolines and a New Synthesis of Unsymmetrical 2,5-Di-substituted 1,3,4-Thiadiazoles" J. Chem. Soc. Perkin Trans. I (1982), pp. 1987-1991.
Moss et al., "Thiadiazoles and Thiadiazolines. Part 4.(1) Acetylation, Hydrolsis, and Cyclocondensations of Δ2-1,3,4-Thiadiazoline-α-carboxamidines", J. Chem. Soc. Perkin Trans. I (1982), pp. 1993-1982.
Newman, et al., "The therapeutic potential of a series of orally bioavailable anti-angiogenic microtubule disruptors as therapy for hormone-independent prostate and breast cancers." British J. of Cancer. 97 (2007): pp. 1673-1682.
Shi, et al., "Cell Type Variation in Responses to Antimitotic Drugs that Target Microtubules and Kinesin-5." Cancer Research. vol. 68, No. 9 (May 1, 2008): pp. 3269-3276.
Steegmaier, et al. "BI 2536, a Potent and Selective Inhibitor of Polo-like Kinase 1, Inhibits Tumor Growth In Vivo." Current Biology, 17 (Feb. 20, 2007): pp. 316-322.
Stephenson, et al. "Phase I Multicenter Study to Asses the Safety, Tolerability, and Pharmacokinetics of AZD4877 Administered Twice Weekly in Adult Patients with Advanced Solid Malignanicies" 2008 ASCO Poster, J. Clin. Oncol. 26:May 20, 2008 (suppl; abstr 2516).
Wood, et al. "Past and future of the mitotic spindle as an oncology treatment." Current Opinion in Pharmacology. vol. 1, Issue 4 (Aug. 1, 2001): pp. 370-377.
2006 EJC Poster: Broker, L.E., et al. "The novel oral taxanes BMS275183 has a favorable activity and toxicity profile in a twice weekly schedule; Preliminary findings from an extended phase I trial." EJC Suppl. 2006 Abstract 644, p. 194.
El-Khouciry et al., 2006 ASCO poster entitled "A Randomized Phase II Non-Comparative Study of Ispinesib Given Weekly or Every Three weeks in Metastatic Colorectal Cancer", www.cytokinetics.com/pdf/SBposter_TS2.pdf.
Lonial, S., et al. American Society of Hematology Annual Meeting 2011, Abstract 2935. "The Novel KSP Inhibitor ARRY-520 Demonstrates Single-Agent Activity in Refractory Myeloma: Results From a Phase 2 Trial in Patients with Relapsed/Refractory Multiple Myeloma (MM)." http://www.arraybiopharma.com/_documents/Publication/PubAttachment494.pdf.
Shah, J.J, et al. American Society of Hematology Annual Meeting 2011, Abstract 1860. "ARRY-520 Shows Durable Responses in Patients with Relapsed/Refractory Multiple Myeloma in a Phase 1 Dose-Escalation Study." http://www.arraybiopharma.com/_documents/Publication/PubAttachment493.pdf.
Woessner, Rich, et al. AACR 2009, Abstract 4703. "In vivo and Pharmacodynamic Profiling of the KSP Inhibitor ARRY-520 Supports Potent Activity in Hematological Cancers and Drug Resistant Tumors." http://www.arraybiopharma.com/_documents/Publication/PubAttachment336.pdf.
Heath, et al., "A Phase I Dose Escalation Trial of Ispinesib (SB-715992) Administered Days 1-3 of a 21-day Cycle in Patients with Advanced Solid Tumors", www.cytokinetics.com/pdf/HeathNc16785051906/ASCO Poster (May 23, 2006).
Jackson, et al., "A Pharmacodynamic Marker of Mitosis Demonstrates the Anti-mitotic Activity of SB-715992, an Inhibitor of the Mitotic Kinesin KSP", www.cytokinetics.com/pdf/AACR Poster (2002).
Johnson, et al., "SB-715992, a Potent and Selctive Inhibitor of KSP Mototic Kinesin Demonstrates Broad-spectrum Activity in Advanced Murine Tumors and Human Tumor Xenografts", www.cytokinetics.com/pdf/AACR Poster (2002).
Lorusso, et al., "A Phase I Study to Determine the Safety and Pharmacokinetics of Intravenous Administration of SB-715992, a Novel Kinesin Spindle Protein (KSP) Inhibitor, on a Once Weekly for Three Consecutive Weeks Schedule in Patients with Refractory Solid Tumors", www.cytokinetics.com/pdf/ECCO Poster (2003).
Philco, et al., "A Phase I-II Open-Label Trial of Ispinesib on an Alternating Dosing Schedule in Chemotherapy-Naive Patients with Locally advanced or Metastatic Breast Cancer (MBC)", www.cytokinetics.com/pdf/ASCO Poster (2008).

\* cited by examiner

METHOD OF TREATMENT USING INHIBITORS OF MITOSIS

BACKGROUND OF THE INVENTION

Field of the Invention

The present invention relates to a method for treating diseases caused by cell division or that are treated by inhibiting mitosis using inhibitors of mitosis on a specific dosing schedule.

Description of the State of Art

Inhibitors of mitosis (also called mitotic inhibitors or anti-mitotics) are important therapeutics for the treatment of diseases, and they are used in treatments for cancer, as well as anti-gout and anti-fungus agents and treating restenosis. These inhibitors of mitosis therapeutics disrupt mitosis such that the cell will no longer divide. In cancer, inhibitors of mitosis can stop cancerous growth and lead to apoptosis or exit from mitosis followed by cell death.

Many inhibitors of mitosis are known. Some inhibitors of mitosis are anti-tubulin agents. Anti-tubulin agents act on tubulin, a protein that is necessary for mitosis. Anti-tubulin agents include vinca alkaloids, taxanes and epothilones. Non-tubulin targeted inhibitors of mitosis have also been investigated as cancer therapeutics. Different inhibitors of mitosis affect different portions of the cell cycle, and sometimes other functions outside of mitosis. For instance, anti-tubulin agents can affect non-mitotic cytoskeletal functions in proliferating cells and in terminally differentiated cells. Peripheral neurotoxicity has been associated with tubulin agents. Thus, different inhibitors of mitosis may have different toxicities.

Vinca alkaloids inhibit microtubule polymerization, which thereby inhibits mitosis. Vinca alkaloids include vinblastine, vincristine, vindesine and vinorelbine. Vinblastine has been used to treat certain kinds of cancer, including Hodgkin's lymphoma, non-small cell lung cancer, breast cancer and testicular cancer. Vincristine has been used to treat certain kinds of cancer, including lymphoma, breast cancer, lung cancer and acute lymphoblastic leukemia. Vinblastine and vincristine have also been used in palliative regimens for some of the major solid tumors (See Wood, Kenneth W., et al. "Past and future of the mitotic spindle as an oncology treatment." *Current Opinion in Pharmacology*. Vol. 1, Issue 4 (Aug. 1, 2001): pp. 370-377). Vindesine has been used to treat certain kinds of cancer, including leukemia, lymphoma, melanoma, breast cancer and lung cancer. Vinorelbine has been used to treat certain kinds of cancer, including breast cancer and non-small cell lung cancer.

Taxanes stabilize microtubules, thereby inactivating the microtubule function of a cell and inhibiting cell division. Taxanes include paclitaxel (including Abraxane) and docetaxel. Paclitaxel is used to treat certain kinds of cancer, including lung cancer, ovarian cancer, breast cancer and advanced forms of Kaposi's sarcoma. Docetaxel is used to treat certain kinds of cancer, including breast cancer, ovarian cancer and non-small cell lung cancer. New taxanes are also in development, for example BMS275183 (See 2006 EJC Poster: Broker, L. E., et al. "The novel oral taxanes BMS275183 has a favorable activity and toxicity profile in a twice weekly schedule; Preliminary findings from an extended phase I trial." *EJC Suppl.* 2006 Abstract 644, p. 194).

Additionally, colchicine is an inhibitor of mitosis that acts as an anti-tubulin agent. Colchicine inhibits mitosis by inhibiting microtubule polymerization. Colchicine is used to treat gout.

Epothilones are a class of microtubule-stabilizing chemotherapeutic agents with activity in paclitaxel-resistant cancer cell lines (See Denduluri, Neelima, et al. "Phase II trial of ixabepilone, an epothilones B analog, given daily for three days every three weeks, in metastatic breast cancer." *Invest. New Drugs*. 25 (Aug. 25, 2006): pp. 63-67). Epothilones include epothilone A, epothilone B, epothilone D and the epothilone analog ixabepilone. Ixabepilone has been approved for the treatment of aggressive metastatic or locally advanced breast cancer no longer responding to currently available chemotherapies.

Dolastatin and dolastatin analogues are inhibitors of mitosis. These compounds include dolastatin 10, dolastatin 15, synthadotin (or SYN-D or ILX651; see 2004 ASCO Abstract No. 3068, Hammond, L. A., et al. "Phase (Ph) I evaluation of the dolastatin analogue synthadotin (SYN-D; ILX651): Pooled data analysis of three alternate schedules in patients (pts) with advanced solid tumors." *J. Clin. Oncology*. 2004 Suppl. Abstract 3068 14s (2004)), LU103793 and cemadotin.

Aurora kinases, including Aurora A, Aurora B and Aurora C, are serine/threonine kinases that function in mitosis. Aurora kinases have been targeted as inhibitors of mitosis. Aurora A has its function in the prophase of mitosis and is required for the centrosomes to function correctly. Aurora B functions in the attachment of the mitotic spindle to the centromere. Aurora kinase inhibitors include AZD-1152, CYC-116, AS-703569 (or R-763), MLN-8054, PHA-739358, AT-9283, SNS-314, AZD-1152-HQPA, MLN-8237, KW-2449, PF-3814735, ENMD-2076 (or ENMD-981693), PHA-739385, MK-0457 (or VX-680) and MK-5108 (or VX-689). For more, see: Gautschi, Oliver, et al. "Aurora Kinases as Anticancer Drug Targets." *Clin. Cancer Res.* 14(6) (Mar. 15, 2008): pp. 1639-48.

Polo-like kinases ("Plks"), including polo-like kinase 1 ("Plk1"), polo-like kinase 2 ("Plk2"), polo-like kinase 3 ("Plk3") and polo-like kinase 4 ("Plk4"), are involved in the formation and changes in the mitotic spindle and in the activation of CDK/cyclin complexes during mitosis. Polo-like kinases have been targeted as inhibitors of mitosis. Polo-like kinase inhibitors include ON-01910Na (or ON-1910Na or Onc-01910), BI-2536 (See: Steegmaier, Martin, et al. "BI 2536, a Potent and Selective Inhibitor of Polo-like Kinase 1, Inhibits Tumor Growth In Vivo." *Current Biology*, 17 (Feb. 20, 2007): pp. 316-322) and GSK-461364 (or GSK-461364A).

Kinesins are a type of motor protein. Mitotic kinesins are enzymes essential for assembly and function of the mitotic spindle. Mitotic kinesins play essential roles during all phases of mitosis. During mitosis, kinesins organize the microtubules into the bipolar structure that is the mitotic spindle Inhibition of mitotic kinesin causes malformation or dysfunction of the mitotic spindle, frequently resulting in cell cycle arrest and apoptosis (cell death).

Among the identified mitotic kinesins is kinesin spindle protein ("KSP"). During mitosis, KSP associates with microtubules of the mitotic spindle Inhibition of KSP prevents spindle pole separation during the prometaphase, giving rise to monopolar spindles causing mitotic arrest and induction of programmed cell death. Human KSP is also called HsEg5.

United States Patent Application Publication 2006/0100161 describes compounds including 2-(3-aminopropyl)-5-(3-fluorophenyl)-N-(2-methoxyethyl)-N-methyl-2-phenyl-1,3,4-thiadiazole-3(2H)-carboxamide (hereinafter "Compound 1"), 2-(3-aminopropyl)-5-(3-fluorophenyl)-N-methoxy-N-methyl-2-phenyl-1,3,4-thiadiazole-3(2H)-carboxamide (hereinafter "Compound 2"), 2-(3-aminopropyl)-5-(2,5-difluorophenyl)-N-methoxy-N-methyl-2-phenyl-1,3,4-thiadiazole-3(2H)-carboxamide (hereinafter "Compound 3"), (S)-2-(3-aminopropyl)-5-(2,5-difluorophenyl)-N-methoxy-N-methyl-2-phenyl-1,3,4-thiadiazole-3(2H)-carboxamide (hereinafter "Compound 4"), (R)-2-(3-aminopropyl)-5-(2,5-difluorophenyl)-N-methoxy-N-methyl-2-phenyl-1,3,4-thiadiazole-3(2H)-carboxamide (hereinafter "Compound 5"), and 2-(3-aminopropyl)-5-(2,5-difluorophenyl)-N-hydroxy-N-methyl-2-phenyl-1,3,4-thiadiazole-3(2H)-carboxamide (hereinafter "Compound 6"). Compounds 1, 2, 3, 4, 5 and 6 (collectively the "'161 KSP Inhibitors") are KSP inhibitors.

KSP inhibitors include ispinesib (or SB-715992 or CK-0238273; See 2008 ASCO Poster: "A Phase I-II Open-Label Trial of Ispinesib on an Alternating Dosing Schedule in Chemotherapy-Naïve Patients with Locally Advanced or Metastatic Breast Cancer (MBC)." www.cytokinetics.com/pdf/ASCO2008A.pdf), the '161 KSP Inhibitors, AZD-4877, CRx-026, SB-743921 (SB-921), MK-0731, EMD-534085 and ARQ 621. Ispinesib has been tested in a wide range of tumor types and is being tested in human clinical trials.

Among the other motor proteins that act during mitosis, small molecule inhibitors have also been described for centromere associated protein E ("CENP-E"). CENP-E is a motor protein (See Chan, G. K. T., et al. "Characterization of the Kinetochore Binding Domain of CENP-E Reveals Interactions with the Kinetochore Proteins CENP-F and hBUBR1." *J. Cell Biology*. Vol. 143, No. 1 (Oct. 5, 1998): pp. 49-63) and can be classified as a type of mitotic kinesin. CENP-E inhibitors include GSK-295 (or GSK-923295).

Many inhibitors of mitosis have been tested as therapeutics for the treatment of diseases. Many non-tubulin inhibitors of mitosis have been tested clinically as therapeutics. Various dosing schedules have been used in these tests of inhibitors of mitosis. There remains a need for effective dosing schedules for inhibitors of mitosis that allows potent biological activity with manageable toxicity. There remains a particular need for effective dosing schedules for inhibitors of mitosis that allows potent anti-cancer activity with manageable toxicity.

SUMMARY OF THE INVENTION

Surprisingly, it has been found that two doses between the biologically effective dose and the maximum tolerated dose of an inhibitor of mitosis in a dosing cycle that allows for the recovery or subsiding of side effects, wherein the second dose is administered 24 to 48 hours after the first dose may be used to treat diseases caused by cell division or that are treated by inhibiting mitosis.

In one aspect, the present invention relates to a method for treating cancer using inhibitors of mitosis on a dosing schedule.

Another aspect of the present invention provides a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 24 to 48 hours after the first dose.

Another aspect of the present invention provides a method for treating diseases caused by cell division or that are treated by inhibiting mitosis by administering two doses of an inhibitor of mitosis between the biologically effective dose and the maximum tolerated dose in a 14 to 21 day dosing cycle, wherein the first dose is administered on day one of the dosing cycle and the second dose is administered on day two or three of the dosing cycle.

Another aspect of the present invention provides a method of treating a hyperproliferative disease or gout by administering two doses of an inhibitor of mitosis between the biologically effective dose and the maximum tolerated dose in a 14 to 21 day dosing cycle, wherein the first dose is administered on day one of the dosing cycle and the second dose is administered on day two or day three of the dosing cycle.

Another aspect of the present invention provides a method of treating cancer by administering two doses of an inhibitor of mitosis between the biologically effective dose and the maximum tolerated dose in a 14 to 21 day dosing cycle, wherein the first dose is administered on day one of the dosing cycle and the second dose is administered on day two or day three of the dosing cycle.

Another aspect of the present invention provides a method of treating cancer by administering to a patient in need two doses of an inhibitor of mitosis selected from the '161 KSP Inhibitors between the biologically effective dose and the maximum tolerated dose in a 14 to 21 day dosing cycle, wherein the first dose is administered on day one of the dosing cycle and the second dose is administered on day two or three of the dosing cycle.

Another aspect of the present invention provides a method for treating a patient afflicted with diseases caused by cell division or that are treated by inhibiting mitosis comprising administering an inhibitor of mitosis in two doses to the patient over a dosing cycle of 14 to 21 days, wherein a first dose is administered on day one of the dosing cycle, and a second dose is administered on day two or day three of the dosing cycle, and wherein the doses comprise a composition containing between the biologically effective dose and the maximum tolerated dose of the inhibitor.

Another aspect of the present invention provides the use of an inhibitor of mitosis for the preparation of a pharmaceutical composition for the treatment of diseases caused by cell division or that are treated by inhibiting mitosis comprising administering the composition to a patient in need over a 14 to 21 day dosing cycle a first dose of the inhibitor on day one of the dosing cycle, followed by a second dose of the inhibitor on day two or three of the dosing cycle, wherein the composition comprises between the biologically effective dose and the maximum tolerated dose of the inhibitor.

DETAILED DESCRIPTION OF THE INVENTION

Figure 1:
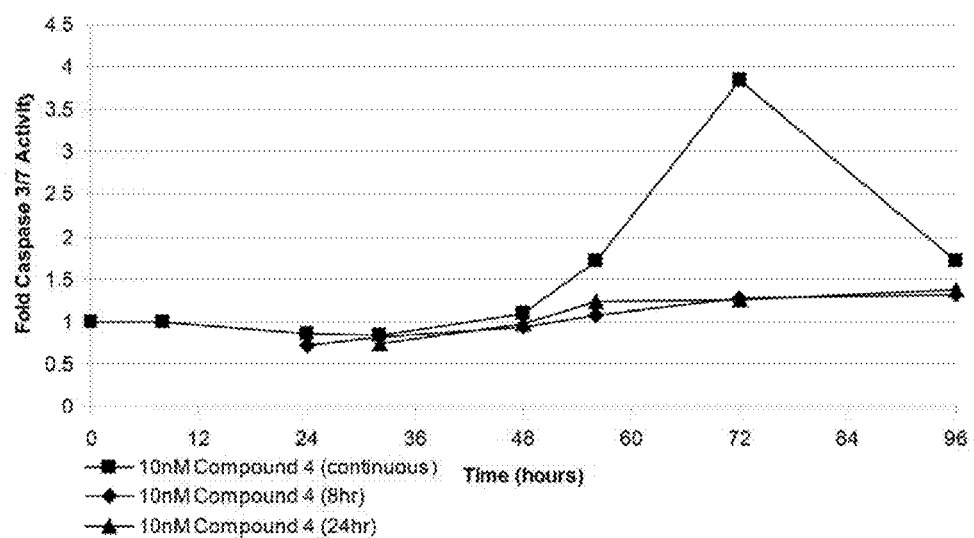
FIG. 1 shows an apoptosis washout experiment.

Reference will now be made in detail to certain embodiments of the invention. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer including melanoma, head and neck cancer, multiple myeloma and acute myeloid leukemia.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

Methods of Treating

The present invention provides a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 24 to 48 hours after the first dose.

Administering an inhibitor of mitosis to cells puts the cells into mitotic arrest. However, mitotic arrest does not necessarily lead the cells to apoptosis or result in antitumor efficacy (See, for example: Shi, Jue, et al. "Cell Type Variation in Responses to Antimitotic Drugs that Target Microtubules and Kinesin-5." *Cancer Research*. 68(9) (May 1, 2008): pp. 3269-76; and 2002 AACR Poster: "A Pharmacodynamic marker of mitosis demonstrates the antimitotic activity of SB-715992, an inhibitor of the mitotic kinesin KSP." www.cytokinetics.com/pdf/AACR_2002_Poster_1336.pdf). It has been found that the cells must stay in arrest for a duration of time before apoptosis peaks (See FIG. 1). The duration of time needed for apoptosis is variable between cell types and types of tumors (See FIGS. 2 and 3). Also, administering two doses instead of one dose increases the duration of the biological effect (See FIGS. 4 and 5), which in the case of inhibitors of mitosis increases the duration and magnitude of apoptosis (See FIGS. 6 and 7). Therefore, an appropriate dosing schedule of an inhibitor of mitosis inhibitor should keep the cells in arrest for an appropriate duration of time to be effective.

Administering an inhibitor of mitosis to cells interferes with mitosis. For example, administering a KSP inhibitor increases the amount of monopolar spindles. However, a minimum amount of the inhibitor must be administered in order to achieve the desired biological response (See FIG. 8). Therefore, an appropriate dosing schedule of an inhibitor of mitosis must achieve a biologically effective dose of the inhibitor to be effective. The biologically effective dose of a KSP inhibitor is the dose of the inhibitor that results in the appearance of arrested, monopolar spindles. These can be seen by immunohistochemical techniques (See FIGS. 4, 5 and 8). The biologically effective dose of other inhibitors of mitosis will result in mitotic aberrations consistent with their target profile.

If the dosing schedule fails to reach the biologically effective dose, then the proper biological response will not transpire. Also, if the dosing schedule fails to hold the cells in arrest long enough, the cells may not go to apoptosis. Therefore, an effective dosing schedule of an inhibitor of mitosis must be dosed at least at the biologically effective dose to get the intended biological effect (i.e., mitotic arrest), as well as, being dosed for a period of time long enough to keep the cells in arrest and induce apoptosis (See FIGS. 4-9 and 17-19).

Figure 16:
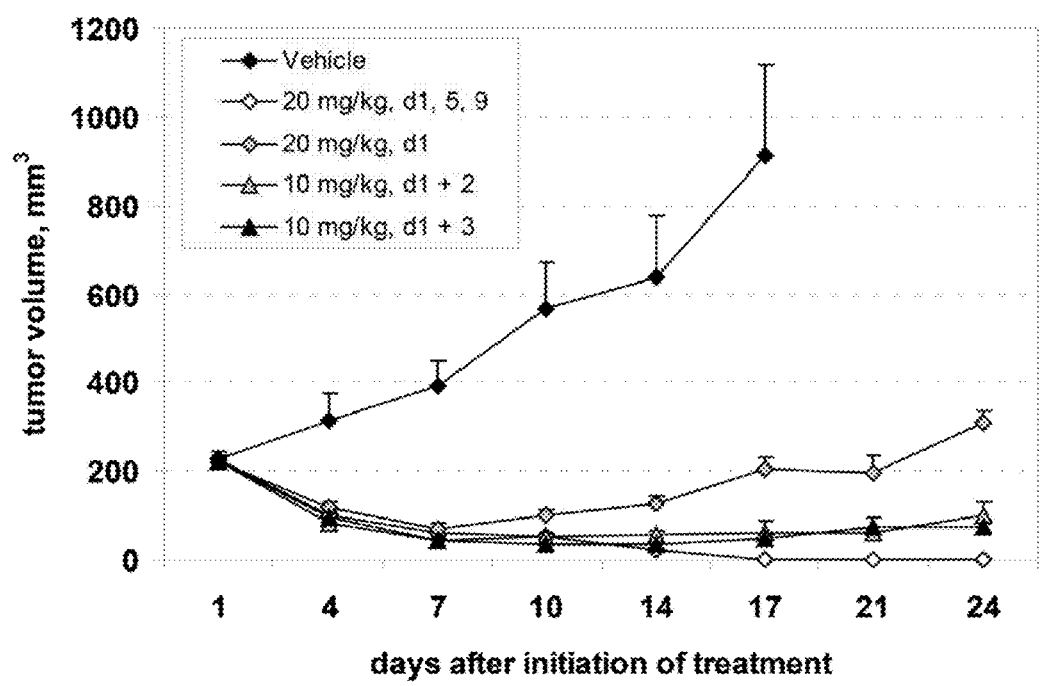
FIG. 16 shows a TGI experiment in nude mice with subcutaneous HT-29 xenografts.

It has been found that a split dose divided over two days may be more efficacious than the same total dose given on one day (See FIG. 16).

For tumors in which cells rapidly enter apoptosis following mitotic block (See FIG. 3), mitotic arrest (See FIG. 17) or apoptosis (See FIG. 18) may not directly correlate with the enhanced efficacy for inhibiting tumor growth on a divided dose schedule (See FIG. 16). In such cases, the fewer cells observed in mitotic arrest and apoptosis may reflect the rapid cell death, such that they are no longer detectable in the tumor. However, the amount of cells with bipolar spindles, indicative of normally cycling cells in mitosis, may inversely correlate with enhanced efficacy (See FIG. 19). In such cases, fewer cells with bipolar spindles indicate a more complete mitotic block, with fewer cells escaping the block and re-entering the cell cycle.

One embodiment of the present invention provides a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects.

Another embodiment of the present invention provides a method for treating diseases caused by cell division or that are treated by inhibiting mitosis by administering a dosing cycle comprising two doses of an inhibitor of mitosis selected from the group consisting of the '161 KSP Inhibitors, wherein the doses are between the biologically effective dose and the maximum tolerated dose, wherein the second dose is administered 12 to 60 hours after the first dose, and wherein the length of the dosing cycle allows for the recovery or subsiding of side effects.

The present invention is directed to treating diseases caused by cell division or that are treated by inhibiting mitosis. Inhibitors of mitosis can be used to treat a variety of diseases, including hyperproliferative diseases and gout. Hyperproliferative diseases include cancer, autoimmune disease, arthritis, graft rejection, inflammatory bowel disease, or proliferation induced after a medical procedure.

In certain embodiments, the invention provides a method for treating cancer. More particularly, cancers that may be treated by the compositions and methods of the invention include, but are not limited to: Soft Tissue Cancers: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood and bone marrow (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. The term "cancerous cell" as provided herein, includes a cell afflicted by any one of the above identified conditions.

In certain embodiments, the present invention provides a method of treating diseases caused by cell division or that are treated by inhibiting mitosis. In certain embodiments, the present invention provides a method of treating solid tumors. The solid tumors include tumors of the skin, breast, brain, cervical carcinomas, testicular carcinomas, etc. In certain embodiments, the solid tumors are selected from breast cancer, colorectal cancer, non-small cell lung cancer, pancreatic cancer, bladder cancer, salivary gland cancer (adenoid cystic), esophageal cancer, mesothelioma cancer, and mixed small cell lung cancer/non-small cell lung cancer.

In certain embodiments, the present invention provides a method of treating diseases caused by cell division or that are treated by inhibiting mitosis. In certain embodiments, the present invention provides a method of treating hematological tumors. The hematological tumors include lymphomas, leukemia, multiple myeloma and the like. In certain embodiments, the present invention provides a method of treating lymphomas, leukemia or multiple myeloma. In further embodiments, a method of treating advanced myeloid leukemia, or relapsed or refractory multiple myeloma is provided.

There are a multitude of variables when developing an effective dosing schedule. Particularly with inhibitors of mitosis, dosing needs to continue for a period of time long enough and at a sufficient exposure level to be biologically effective. It has been found that two doses of inhibitors of mitosis can provide this effective dosing schedule.

The first dose is administered starting the timing of the dosing cycle. This first dose is said to be on day one of the dosing cycle. The present invention provides two doses of an inhibitor of mitosis, wherein the second dose is on day two or day three of the dosing cycle. Alternatively, dose two is within 24 to 48 hours of the first dose. This aspect of the present method allows for the dosing schedule to hold the cells in mitotic arrest long enough to promote apoptosis or exit of mitosis.

Certain embodiments provide that the second dose is administered 24 to 48 hours after the first dose. The timing of this second dose need not be exactly 24 to 48 hours after the first dose. This is just a convenient way of saying the second dose should be administered one or two days after the first dose. Therefore, the second dose is administered approximately 24 to 48 hours after the first dose. This second dose may be administered 12 to 60 hours after the first dose.

Certain embodiments provide that the second dose is administered 24 hours after the first dose. The timing of this second dose need not be exactly 24 hours after the first dose. This is just a convenient way of saying the second dose should be administered the following day. Therefore, the second dose is administered approximately 24 hours after the first dose. This second dose may be administered 12 to 36 hours after the first dose.

In one embodiment of the present invention, the second dose is administered on day two of the dosing cycle. In another embodiment, the second dose is administered 24 hours after the first dose.

In one embodiment of the present invention, the second dose is administered on day two of the dosing cycle. In another embodiment, the second dose is administered 24 hours after the first dose. These particular embodiments have the advantage of being dosed on back to back days, which allows for more convenience to the patients. It is preferable to have a convenient dosing schedule for patients to increase patient compliance with the method of treatment. This is especially true of therapeutics that are administered to patients via intravenous injection, as additional doses may require additional visits to a hospital or doctor to receive the injections.

Certain embodiments provide that the second dose is administered 48 hours after the first dose. The timing of this second dose need not be exactly 48 hours after the first dose. This is just a convenient way of saying the second dose should be administered two days later. Therefore, the second dose is administered approximately 48 hours after the first dose. This second dose may be administered 36 to 60 hours after the first dose.

Many types of inhibitors of mitosis are known, including vinca alkaloids, taxanes, epothilones, dolastatin and dolastatin analogues, aurora kinases, polo-like kinases, and mitotic kinesin inhibitors.

In certain embodiments of the present invention, the inhibitor of mitosis is selected from the group consisting of vinca alkaloids, taxanes, epothilones, dolastatin and dolastatin analogues, aurora kinase inhibitors, polo-like kinase inhibitors, and mitotic kinesin inhibitors.

In certain embodiments of the present invention, the inhibitor of mitosis is a mitotic kinesin inhibitor. In a further embodiment of the present invention, the inhibitor of mitosis is a CENP-E inhibitor or a KSP inhibitor. In a further embodiment of the present invention, the inhibitor of mitosis is a KSP inhibitor.

In certain embodiments of the present invention, the inhibitor of mitosis is selected from the group consisting of GSK-295, ispinesib, the '161 KSP Inhibitors, AZD-4877, CRx-026, SB-743921 (SB-921), MK-0731, EMD-534085 and ARQ 621.

In certain embodiments of the present invention, the inhibitor of mitosis is a KSP inhibitor.

In certain embodiments of the present invention, the inhibitor of mitosis is selected from the group consisting of ispinesib, the '161 KSP Inhibitors, AZD-4877, CRx-026, SB-743921 (SB-921), MK-0731, EMD-534085 and ARQ 621.

In certain embodiments of the present invention, the inhibitor of mitosis is selected from ispinesib, the '161 KSP Inhibitors and AZD-4877.

In certain embodiments of the present invention, the inhibitor of mitosis is selected from the group consisting of the '161 KSP Inhibitors. In a further embodiment of the present invention, the inhibitor of mitosis is Compound 1. In a further embodiment of the present invention, the inhibitor of mitosis is Compound 2. In a further embodiment of the present invention, the inhibitor of mitosis is Compound 3. In a further embodiment of the present invention, the inhibitor of mitosis is Compound 4. In a further embodiment of the present invention, the inhibitor of mitosis is Compound 5. In a further embodiment of the present invention, the inhibitor of mitosis is Compound 6.

In certain embodiments of the present invention, the inhibitor of mitosis is selected from the group consisting of aurora kinase inhibitors, polo-like kinase inhibitors, mitotic kinesin inhibitors and CENP-E inhibitors. In certain embodiments of the present inventions, the inhibitor of mitosis is selected from the group consisting of SU-6668, AZD-1152, CYC-116, AS-703569, MLN-8054, R763, PHA-739358, AT-9283, SNS-314, AZD-1152-HQPA, MLN-8237, KW-2449, PF-3814735, ENMD-2076, PHA-739385, MK-0457, MK-5108, ON-01910Na, BI-2536, GSK-461364, ispinesib, the '161 KSP Inhibitors, AZD-4877, CRx-026, SB-743921 (SB-921), MK-0731, EMD-534085, ARQ 621 and GSK-295.

In certain embodiments of the present invention, the inhibitor of mitosis is selected from the group consisting of vinblastine, vincristine, vindesine, vinorelbine, paclitaxel, docetaxel, Abraxane, colchicine, epothilone A, epothilone B, epothilone D, ixabepilone, dolastatin 10, dolastatin 15, synthadotin, LU103793, cemadotin, SU-6668, AZD-1152, CYC-116, AS-703569, MLN-8054, R763, PHA-739358, AT-9283, SNS-314, AZD-1152-HQPA, MLN-8237, KW-2449, PF-3814735, ENMD-2076, PHA-739385, MK-0457, MK-5108, ON-01910Na, BI-2536, GSK-461364, GSK-295, ispinesib, the '161 KSP Inhibitors, AZD-4877, CRx-026, SB-743921 (SB-921), MK-0731, EMD-534085, ARQ 621 and GSK-295.

In certain embodiments of the present invention, the inhibitor of mitosis is a vinca alkaloid. In a further embodiment, the inhibitor of mitosis is selected from the group consisting of vinblastine, vincristine, vindesine and vinorelbine.

In certain embodiments of the present invention, the inhibitor of mitosis is a taxane. In a further embodiment, the inhibitor of mitosis is selected from the group consisting of paclitaxel, Abraxane and docetaxel.

In certain embodiments of the present invention, the inhibitor of mitosis is colchicine.

In certain embodiments of the present invention, the inhibitor of mitosis is an epothilone. In a further embodiment, the inhibitor of mitosis is selected from the group consisting of epothilone A, epothilone B, epothilone D and ixabepilone.

In certain embodiments of the present invention, the inhibitor of mitosis is dolastatin or a dolastatin analogue. In a further embodiment, the inhibitor of mitosis is selected from the group consisting of dolastatin 10, dolastatin 15, synthadotin, LU103793 and cemadotin.

In certain embodiments of the present invention, the inhibitor of mitosis is an aurora kinase inhibitor. In a further embodiment, the inhibitor of mitosis is selected from the group consisting of SU-6668, AZD-1152, CYC-116, AS-703569, MLN-8054, R763, PHA-739358, AT-9283, SNS-314, AZD-1152-HQPA, MLN-8237, KW-2449, PF-3814735, ENMD-2076, PHA-739385, MK-0457 and MK-5108.

In certain embodiments of the present invention, the inhibitor of mitosis is a polo-like kinase inhibitor. In a further embodiment, the inhibitor of mitosis is selected from the group consisting of ON-01910Na, BI-2536 and GSK-461364.

In certain embodiments of the present invention, the inhibitor of mitosis is a CENP-E inhibitor. In a further embodiment, the inhibitor of mitosis is GSK-295.

As discussed above, the proper amount of inhibitor of mitosis must be dosed in order to reach the desired biological effect. Thus, an effective dosing schedule will dose at least a minimum amount that reaches the desired biological effect, or biologically effective dose. However, the dose should not be so high as to outweigh the benefit of the biological effect with unacceptable side effects. Therefore, an effective dosing schedule will dose no more than the maximum tolerated dose ("MTD"). The present invention provides a method of treating a patient with a dosing schedule that includes two doses of an inhibitor of mitosis, wherein the two doses of the inhibitor are between the biologically effective dose and the maximum tolerated dose.

The maximum tolerated dose is defined as the highest dose that produces an acceptable incidence of dose-limiting toxicities ("DLT"). Doses that cause an unacceptable rate of DLT are considered non-tolerated. Typically, the MTD for a particular schedule is established in phase 1 clinical trials. These are usually conducted in patients by starting at a safe starting dose of ⅒ the severe toxic dose ("STD10") in rodents (on a mg/m² basis) and accruing patients in cohorts of three, escalating the dose according to a modified Fibonacci sequence in which ever higher escalation steps have ever decreasing relative increments (e.g., dose increases of 100%, 65%, 50%, 40%, and 30% to 35% thereafter). The dose escalation is continued in cohorts of three patients until a non-tolerated dose is reached. The next lower dose level that produces an acceptable rate of DLT is considered to be the MTD.

Also, the MTD of an inhibitor of mitosis varies depending on the inhibitor, species, formulation and dosing schedule. For instance, dosing only on day one versus days one and two versus days one through three over a seven, fourteen, twenty-one or twenty-eight day dosing cycle may all have different MTDs. However, as discussed above, an effective dosing schedule needs to dose the inhibitor high enough to be biologically effective and long enough to keep the cells in mitotic arrest. Dosing on day one only may reach the biologically effective dose, but may not be long enough to get the cells to apoptosis. Alternatively, dosing days one through three may dose long enough, but may not dose high enough to reach the biologically effective dose. This may be due to the MTD of dosing for three days being lower than the biologically effective dose. Thus, an effective dosing schedule will have an MTD equal to or greater than the biologically effective dose.

In one embodiment of the present invention, the two doses of the inhibitor of mitosis are administered between the biologically effective dose and the maximum tolerated dose.

In another embodiment of the present invention, the two doses of the inhibitor of mitosis are administered at the maximum tolerated dose.

Typically when treating a hyperproliferative disease such as cancer, patients are dosed at the MTD of a particular compound so that the maximum benefit in the treatment can be reached. Accordingly, one embodiment of the present invention provides a method of treating cancer by administering two doses of an inhibitor of mitosis, wherein the two doses are the maximum tolerated dose of the inhibitor.

In one embodiment of the present invention, the second dose is administered on day three of the dosing cycle. In another embodiment, the second dose is administered 48 hours after the first dose.

A dosing cycle (or dosing schedule) is established so that after the first cycle is completed additional cycles may be administered until such treatment is no longer necessary or effective. One of the factors in determining the length of a dosing cycle is allowing for the recovery or subsiding of side effects. After administering a pharmaceutical composition or therapeutic, particularly an inhibitor of mitosis, patients may experience side effects. Depending on the type of side effects, a recovery or subsiding of side effects may be necessary. This recovery or subsiding of side effects may take time, which in turn can control the length of the dosing cycle before a second cycle may begin.

One of the side effects of inhibitors of mitosis, and particularly KSP inhibitors, is acute neutropenia. Neutropenia is a hematological disorder characterized by an abnormally low number of neutrophil granulocytes, a type of white blood cell. Generally, patients who experience this type of side effect from an inhibitor of mitosis (or KSP inhibitor) recover or the neutropenia subsides as time passes without additional doses of the inhibitor.

When administering a single dose of a KSP inhibitor each cycle, many patients recover from the side effects or the side effects subside on day 14 to day 21 of the dosing cycle. Accordingly, the present invention provides a dosing schedule of 14 to 21 days.

Certain embodiments provide that the dosing cycle is 14 to 21 days. The dosing cycle need not be exactly 14 to 21 days. This is just a convenient way of saying the dosing cycle should be two to three weeks. Therefore, the dosing cycle is approximately 14 to 21 days. The dosing cycle may be 11 to 24 days.

One embodiment of the present invention provides a dosing cycle that allows for the recovery or subsiding of side effects. In one embodiment of the present invention, the dosing schedule is 14 to 21 days.

In another embodiment of the present invention, the dosing schedule is 14 days.

In another embodiment of the present invention, the dosing schedule 11 to 17 days. In a further embodiment, the dosing schedule is 14 days.

In another embodiment of the present invention, the dosing schedule is 21 days.

In another embodiment of the present invention, the dosing schedule is 18 to 24 days. In a further embodiment, the dosing schedule is 21 days.

Certain embodiments of the present invention provide a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 24 to 48 hours after the first dose. In a further embodiment, the two doses are at the maximum tolerated dose.

Another embodiment provides a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 24 hours after the first dose. In a further embodiment, the two doses are at the maximum tolerated dose.

Another embodiment provides a method for treating diseases caused by cell division or that are treated by inhibiting mitosis by administering two doses of an inhibitor of mitosis between the biologically effective dose and the maximum tolerated dose in a dosing cycle that allows for the recovery or subsiding of side effects, wherein the second dose is administered 48 hours after the first dose. In a further embodiment, the two doses are at the maximum tolerated dose.

Certain embodiments of the present invention provide a method for treating diseases caused by cell division or that are treated by inhibiting mitosis by administering two doses of an inhibitor of mitosis between the biologically effective dose and the maximum tolerated dose in a 14 to 21 day dosing cycle, wherein the second dose is administered one or two days after the first dose. In a further embodiment, the two doses are at the maximum tolerated dose.

Another embodiment of the present invention provides a method for treating diseases caused by cell division or that are treated by inhibiting mitosis by administering two doses of an inhibitor of mitosis between the biologically effective dose and the maximum tolerated dose in a 14 to 21 day dosing cycle, wherein the first dose is administered on day one of the dosing cycle and the second dose is administered on day two or day three of the dosing cycle. In a further embodiment, the two doses are at the maximum tolerated dose.

Another embodiment of the present invention provides a method for treating diseases caused by cell division or that are treated by inhibiting mitosis by administering two doses of an inhibitor of mitosis between the biologically effective dose and the maximum tolerated dose in a 14 to 21 day dosing cycle, wherein the first dose is administered on day one of the dosing cycle and the second dose is administered on day two of the dosing cycle. In a further embodiment, the two doses are at the maximum tolerated dose.

Another embodiment of the present invention provides a method for treating diseases caused by cell division or that are treated by inhibiting mitosis by administering two doses of an inhibitor of mitosis between the biologically effective dose and the maximum tolerated dose in a 14 to 21 day dosing cycle, wherein the first dose is administered on day one of the dosing cycle and the second dose is administered on day three of the dosing cycle. In a further embodiment, the two doses are at the maximum tolerated dose.

Another embodiment of the present invention provides a method for treating diseases caused by cell division or that are treated by inhibiting mitosis by administering two doses of an inhibitor of mitosis between the biologically effective dose and the maximum tolerated dose in a 14 day dosing cycle, wherein the first dose is administered on day one of the dosing cycle and the second dose is administered on day two or day three of the dosing cycle. In a further embodiment, the second dose is administered on day two of the dosing cycle. In another further embodiment, the second dose is administered on day three of the dosing cycle. In a further embodiment, the two doses are at the maximum tolerated dose.

Another embodiment of the present invention provides a method for treating diseases caused by cell division or that are treated by inhibiting mitosis by administering two doses of an inhibitor of mitosis between the biologically effective dose and the maximum tolerated dose in a 21 day dosing cycle, wherein the first dose is administered on day one of the dosing cycle and the second dose is administered on day two or day three of the dosing cycle. In a further embodiment, the second dose is administered on day two of the dosing cycle. In another further embodiment, the second dose is administered on day three of the dosing cycle. In a further embodiment, the two doses are at the maximum tolerated dose.

Certain embodiments of the present invention provide a method of treating a hyperproliferative disease or gout by administering two doses of an inhibitor of mitosis between the biologically effective dose and the maximum tolerated dose in a 14 to 21 day dosing cycle, wherein the first dose is administered on day one of the dosing cycle and the second dose is administered on day two or day three of the dosing cycle. In a further embodiment, the dosing cycle is 14 days. In another further embodiment, the dosing cycle is 21 days. In another embodiment, the second dose is administered on day two of the dosing cycle. In yet another embodiment, the second dose is administered on day three of the dosing cycle. In a further embodiment, the two doses are at the maximum tolerated dose.

Certain embodiments of the present invention provide a method of treating a hyperproliferative disease or gout by administering two doses of an inhibitor of mitosis between the biologically effective dose and the maximum tolerated dose in a 14 to 21 day dosing cycle, wherein the second dose is administered 24 to 48 hours after the first dose. In a further embodiment, the dosing cycle is 14 days. In another further embodiment, the dosing cycle is 21 days. In another embodiment, the second dose is administered 24 hours after the first dose. In yet another embodiment, the second dose is administered 48 hours after the first dose. In a further embodiment, the two doses are at the maximum tolerated dose.

Certain embodiments of the present invention provide a method of treating a hyperproliferative disease or gout by administering two doses of an inhibitor of mitosis selected from the group consisting of the '161 KSP Inhibitors between the biologically effective dose and the maximum tolerated dose in a 14 to 21 day dosing cycle, wherein the first dose is administered on day one of the dosing cycle and the second dose is administered on day two or day three of the dosing cycle. In a further embodiment, the dosing cycle is 14 days. In another further embodiment, the dosing cycle is 21 days. In another embodiment, the second dose is administered on day two of the dosing cycle. In yet another embodiment, the second dose is administered on day three of the dosing cycle. In another embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum dose.

Certain embodiments of the present invention provide a method of treating cancer by administering to a patient in need two doses of an inhibitor of mitosis selected from the group consisting of the '161 KSP Inhibitors between the biologically effective dose and the maximum tolerated dose in a 14 to 21 day dosing cycle, wherein the first dose is administered on day one of the dosing cycle and the second dose is administered on day two or three of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 14 day dosing cycle, wherein the first dose is administered on day one of the dosing cycle and the second dose is administered on day two or three of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 14 day dosing cycle, wherein the first dose is administered on day one of the dosing cycle and the second dose is administered on day two of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 14 day dosing cycle, wherein the first dose is administered on day one of the dosing cycle and the second dose is administered on day three of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 21 day dosing cycle, wherein the first dose is administered on day one of the dosing cycle and the second dose is administered on day two or three of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 21 day dosing cycle, wherein the first dose is administered on day one of the dosing cycle and the second dose is administered on day two of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Another embodiment of the present invention provide a method of treating cancer by administering to a patient in need two doses of an inhibitor of mitosis selected from the group consisting of the '161 KSP Inhibitors between the biologically effective dose and the maximum tolerated dose in a 21 day dosing cycle, wherein the first dose is administered on day one of the dosing cycle and the second dose is administered on day three of the dosing cycle. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6. In a further embodiment, the two doses are at the maximum tolerated dose.

Certain embodiments of the present invention provide a method for treating a patient afflicted with diseases caused by cell division or that are treated by inhibiting mitosis comprising administering an inhibitor of mitosis in two doses to the patient over a dosing cycle of 14 to 21 days, wherein a first dose is administered on day one of the dosing cycle, and a second dose is administered on day two or day three of the dosing cycle, and wherein the doses comprise a composition containing between the biologically effective dose and the maximum tolerated dose of the inhibitor. In a further embodiment, the dosing cycle is 14 days. In another further embodiment, the dosing cycle is 21 days. In a further embodiment, the second dose is administered on day two of the dosing cycle. In another further embodiment, the second dose is administered on day three of the dosing cycle. In a further embodiment, the composition comprises the maximum tolerated dose of the inhibitor. In a further embodiment, the disease is a hyperproliferative disease or gout. In a further embodiment, the hyperproliferative disease is cancer. In a further embodiment, the inhibitor of mitosis selected from the group consisting of vinca alkaloids, taxanes, epothilones, dolastatin and dolastatin analogues, aurora kinase inhibitors, polo-like kinase inhibitors and mitotic kinesin inhibitors. In a further embodiment, the inhibitor of mitosis is a KSP inhibitor. In a further embodiment, the inhibitor of mitosis is selected from the group consisting of ispinesib, the '161 KSP Inhibitors, AZD-4877, CRx-026, SB-743921 (SB-921), MK-0731, EMD-534085 and ARQ 621. In a further embodiment, the inhibitor of mitosis is ispinesib, the '161 KSP Inhibitors or AZD-4877. In a further embodiment, the inhibitor of mitosis is selected from the group consisting of the '161 KSP Inhibitors. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6.

Certain embodiments of the present invention provide the use of an inhibitor of mitosis for the preparation of a pharmaceutical composition for the treatment of diseases caused by cell division or that are treated by inhibiting mitosis comprising administering the composition to a patient in need over a 14 to 21 day dosing cycle a first dose of the inhibitor on day one of the dosing cycle, followed by a second dose of the inhibitor on day two or three of the dosing cycle, wherein the composition comprises between the biologically effective dose and the maximum tolerated dose of the inhibitor. In a further embodiment, the dosing cycle is 14 days. In another further embodiment, the dosing cycle is 21 days. In a further embodiment, the second dose is administered on day two of the dosing cycle. In another further embodiment, the second dose is administered on day three of the dosing cycle. In a further embodiment, the composition comprises the maximum tolerated dose of the inhibitor. In a further embodiment, the disease is a hyperproliferative disease or gout. In a further embodiment, the hyperproliferative disease is cancer. In a further embodiment, the inhibitor of mitosis selected from the group consisting of vinca alkaloids, taxanes, epothilones, dolastatin and dolastatin analogues, aurora kinase inhibitors, polo-like kinase inhibitors and mitotic kinesin inhibitors. In a further embodiment, the inhibitor of mitosis is a KSP inhibitor. In a further embodiment, the inhibitor of mitosis is selected from the group consisting of ispinesib, the '161 KSP Inhibitors, AZD-4877, CRx-026, SB-743921 (SB-921), MK-0731, EMD-534085 and ARQ 621. In a further embodiment, the inhibitor of mitosis is ispinesib, the '161 KSP Inhibitors or AZD-4877. In a further embodiment, the inhibitor of mitosis is selected from the group consisting of the '161 KSP Inhibitors. In one embodiment of the present invention, the '161 KSP Inhibitor is Compound 1. In another embodiment of the present invention, the '161 KSP Inhibitor is Compound 2. In another embodiment of the present invention, the '161 KSP Inhibitor is Compound 3. In another embodiment of the present invention, the '161 KSP Inhibitor is Compound 4. In another embodiment of the present invention, the '161 KSP Inhibitor is Compound 5. In another embodiment of the present invention, the '161 KSP Inhibitor is Compound 6.

EXAMPLES

In order to illustrate the invention, the following Examples are included. However, it is to be understood that these Examples do not limit the invention and are only meant to suggest a method of practicing the invention.

Example 1

Apoptosis Washout

HT-29 cells, treated with either vehicle control (DMSO), or 10 nM Compound 4, were seeded in identical 96-well tissue culture plates. After 8 or 24 hours, Compound 4 was removed from HT-29 cells and replaced with fresh growth medium in order to determine whether apoptosis induction could be prevented. Caspase 3/7 activity was measured as reaction product luminescence at the indicated times using CaspaseGlo 3/7 reagent (Promega) and a luminometer. Values are reported as caspase 3/7 activity of Compound 4-treated cells divided by caspase 3/7 activity of DMSO-treated cells. The results are shown in FIG. 1.

Example 2

Apoptosis in HT-29 Following Continuous Treatment with Compound 4

Figure 2:
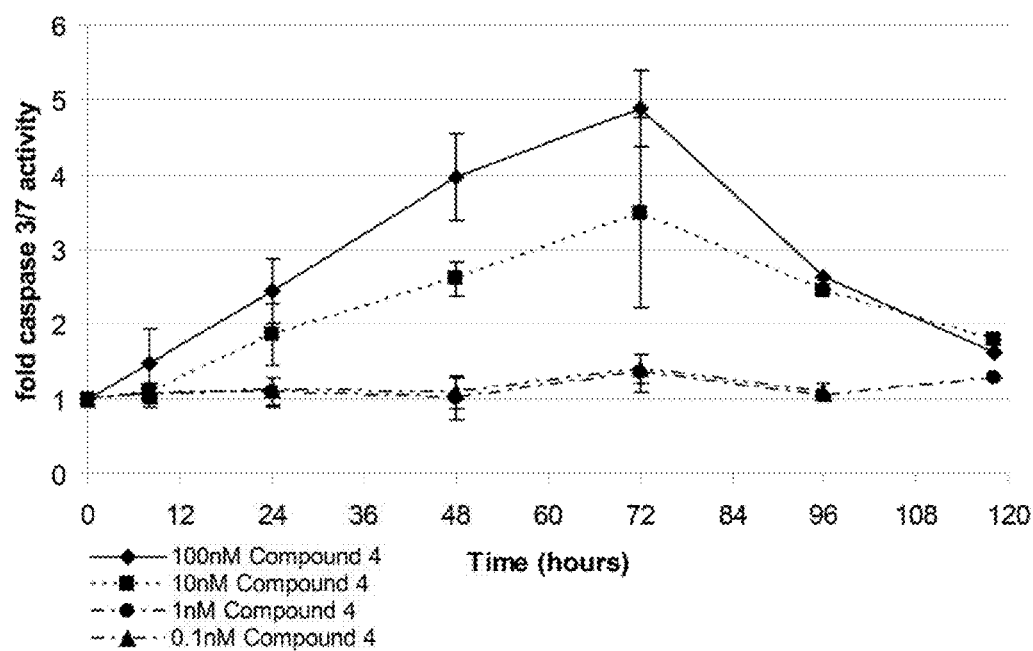
FIG. 2 shows caspase 3/7 activity over time in HT-29 cells in vitro.

HT-29 cells, continuously treated with either vehicle control (DMSO), or 100 nM, 10 nM, 1 nM, or 0.1 nM Compound 4, were seeded in identical 96-well tissue culture plates. Caspase 3/7 activity was measured as luminescent reaction product at the indicated times using CaspaseGlo 3/7 reagent (Promega) and a luminometer. Values are reported as caspase 3/7 activity of Compound 4-treated cells divided by caspase 3/7 activity of DMSO-treated cells. Data include mean and standard deviation values from 4 independent experiments. The results are shown in FIG. 2.

Example 3

Apoptosis in RPMI 8226

Figure 3:
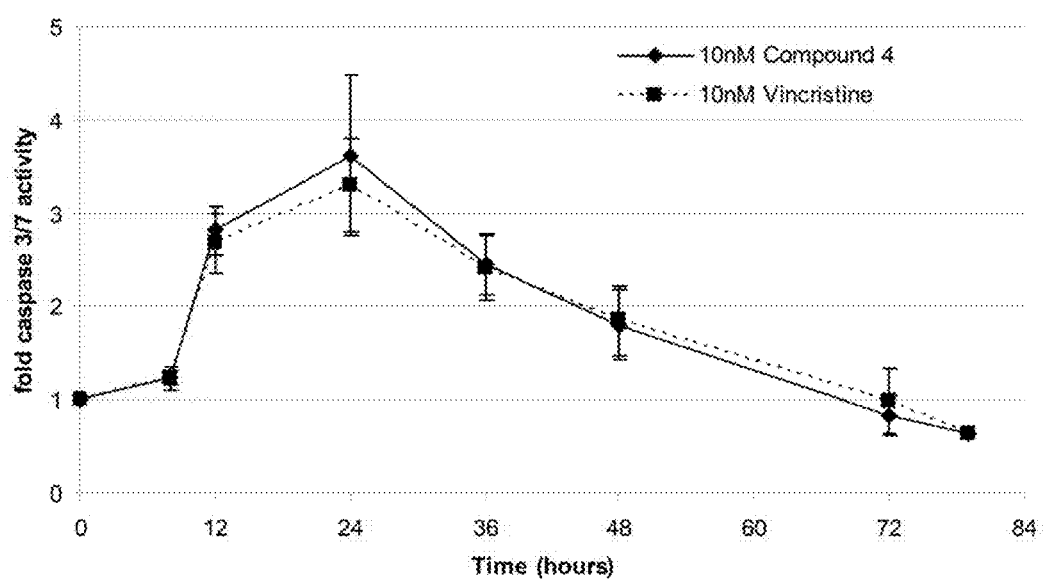
FIG. 3 shows caspase 3/7 activity over time in RPMI 8226 cells in vitro.

RPMI 8226 cells, treated with either vehicle control (DMSO), 10 nM Compound 4, or 10 nM vincristine were seeded in identical 96-well tissue culture plates. Caspase 3/7 activity was measured as luminescent reaction product at the indicated times using CaspaseGlo 3/7 reagent (Promega) and a luminometer. Values are reported as caspase 3/7 activity of drug-treated cells divided by caspase 3/7 activity of DMSO-treated cells. Data include mean and standard deviation values from 4 independent experiments. The results are shown in FIG. 3.

Example 4

Duration of Monopolar Spindles and Magnitude of Apoptosis (HT-29 Xenografts)

Figure 4:
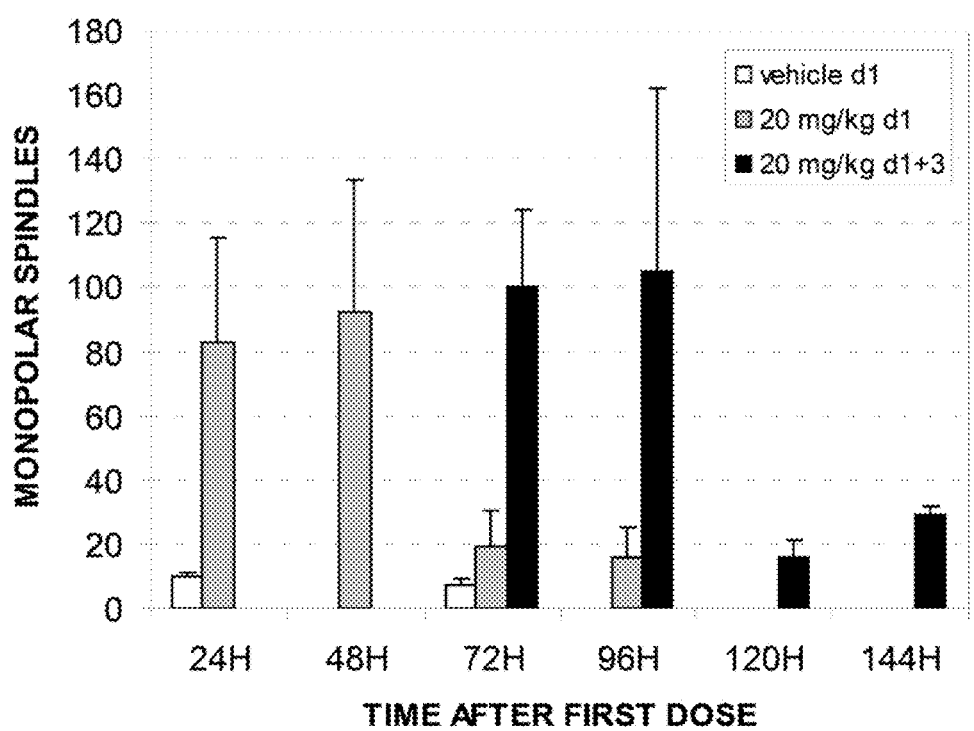
FIG. 4 shows the amount of monopolar spindles in subcutaneous HT-29 xenografts in nude mice at various time points for two different dosing schedules.
Figure 6:
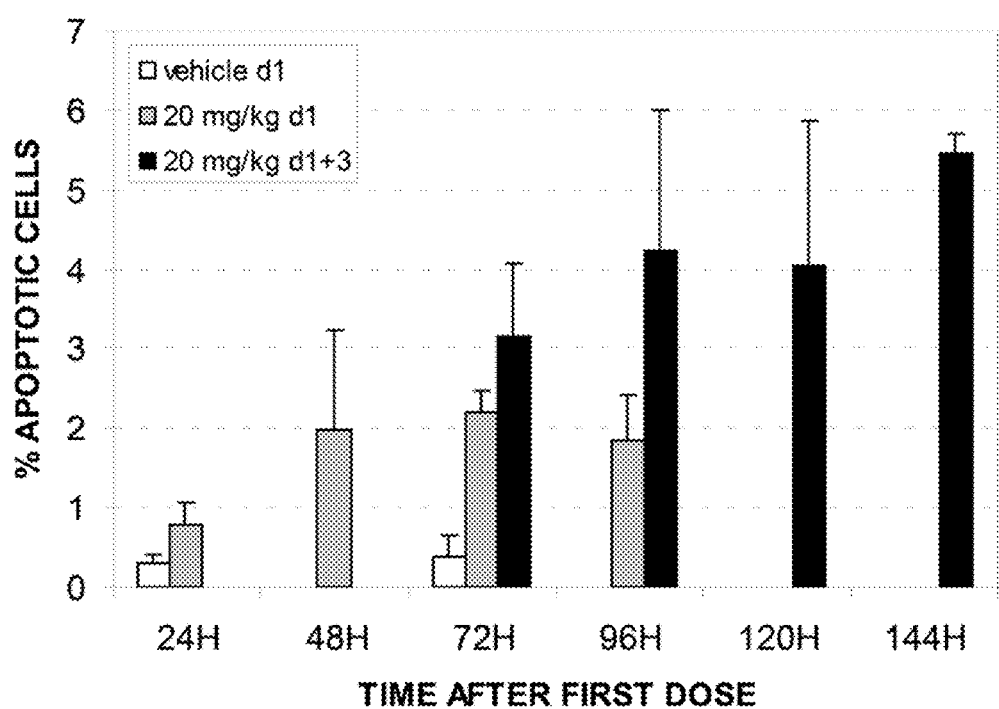
FIG. 6 shows the percentage of apoptotic cells in subcutaneous HT-29 xenografts in nude mice at various time points for two different dosing schedules.

Female nude mice were implanted subcutaneously with $5\times10^6$ HT-29 cells in 100 μL PBS. Ten days later, tumors were measured and mice randomized into groups of three with average tumor volume in each group of approximately 240 mm$^3$. Compound 4 was dissolved in normal saline immediately before dosing. It was determined that 20 mg/kg was the MTD for Compound 4. Dose volume was 10 mL/kg. Dosing was vehicle alone on day 1; and Compound 4 at 20 mg/kg on day 1; and 20 mg/kg on days 1 and 3. At various time points after dosing (24, 48, 72, 96, 120 and 144 hours), mice were euthanized by $CO_2$ inhalation, and the tumors were harvested and immediately placed in formalin. The vehicle control group samples were collected 24 and 72 hours after dosing. The day 1 group samples were collected 24, 48, 72 and 96 hours after that dose. The day 1 and day 3 group samples were collected 72, 96, 120 and 144 hours after the first dose. Paraffin blocks of tumor tissue were prepared by standard procedures. Visualization of monopolar spindles was carried out by staining cut sections with mouse anti-human alpha tubulin primary antibody (clone B-7, Santa Cruz Biotechnology) followed by goat anti-mouse secondary antibody conjugated to Alexafluor 488 (Invitrogen). Nuclei were stained with Hoechst 33342 for cell counting. Spindle structures were manually counted in three 40× areas of each sample, using a fluorescent microscope. Apoptosis was quantitated by manual counting of TUNEL positive cells, also in three 40× areas of each sample (TUNEL staining using the In Situ Cell Death Detection Kit, AP from Roche). The results are shown in FIGS. 4 and 6.

Example 5

Duration of Monopolar Spindles and Magnitude of Apoptosis (HT-29 Xenografts)

Figure 5:
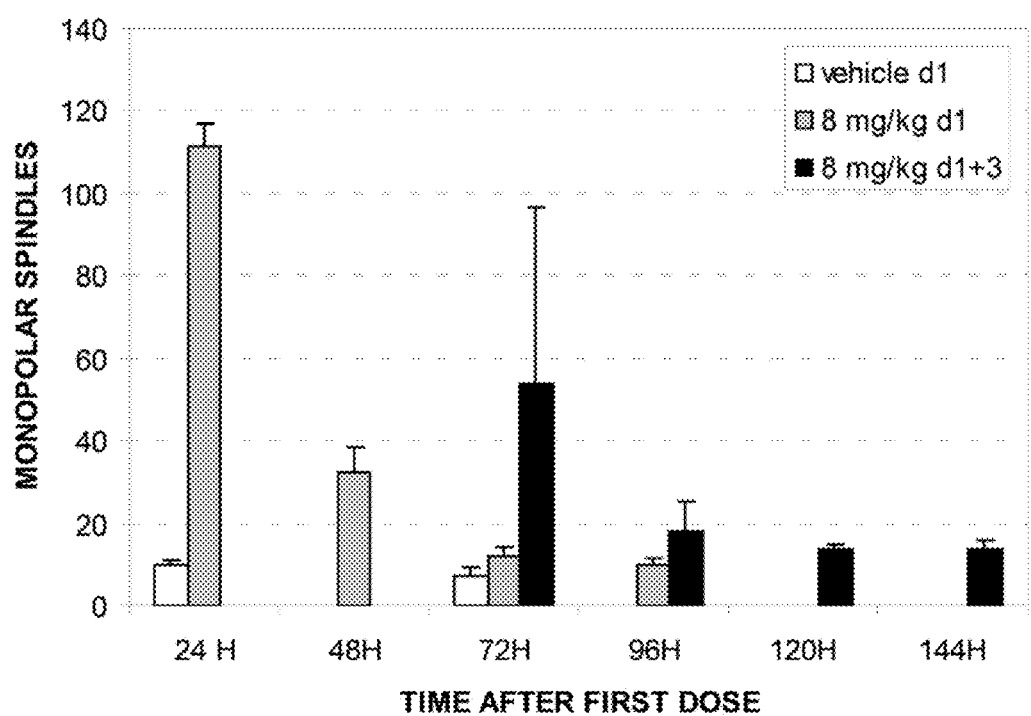
FIG. 5 shows the amount of monopolar spindles in subcutaneous HT-29 xenografts in nude mice at various time points for two different dosing schedules.
Figure 7:
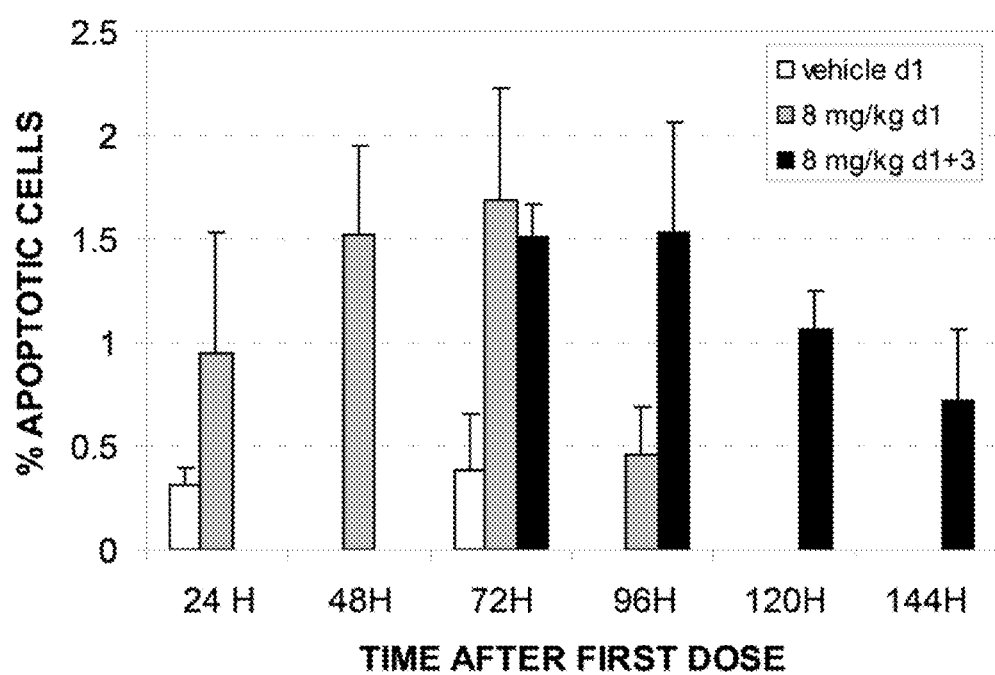
FIG. 7 shows the percentage of apoptotic cells in subcutaneous HT-29 xenografts in nude mice at various time points for two different dosing schedules.

The methods of Example 5 are the same as Example 4, except that the dosing was vehicle alone on day 1; and Compound 4 at 8 mg/kg on day 1; and 8 mg/kg on days 1 and 3. The vehicle control group samples were collected 24 and 72 hours after dosing. The day 1 group samples were collected 24, 48, 72 and 96 hours after that dose. The days 1 and 3 group samples were collected 72, 96, 120 and 144 hours after the first dose. The results are shown in FIGS. 5 and 7.

Example 6

Mitotic Block and Apoptosis (HT-29)

Figure 8:
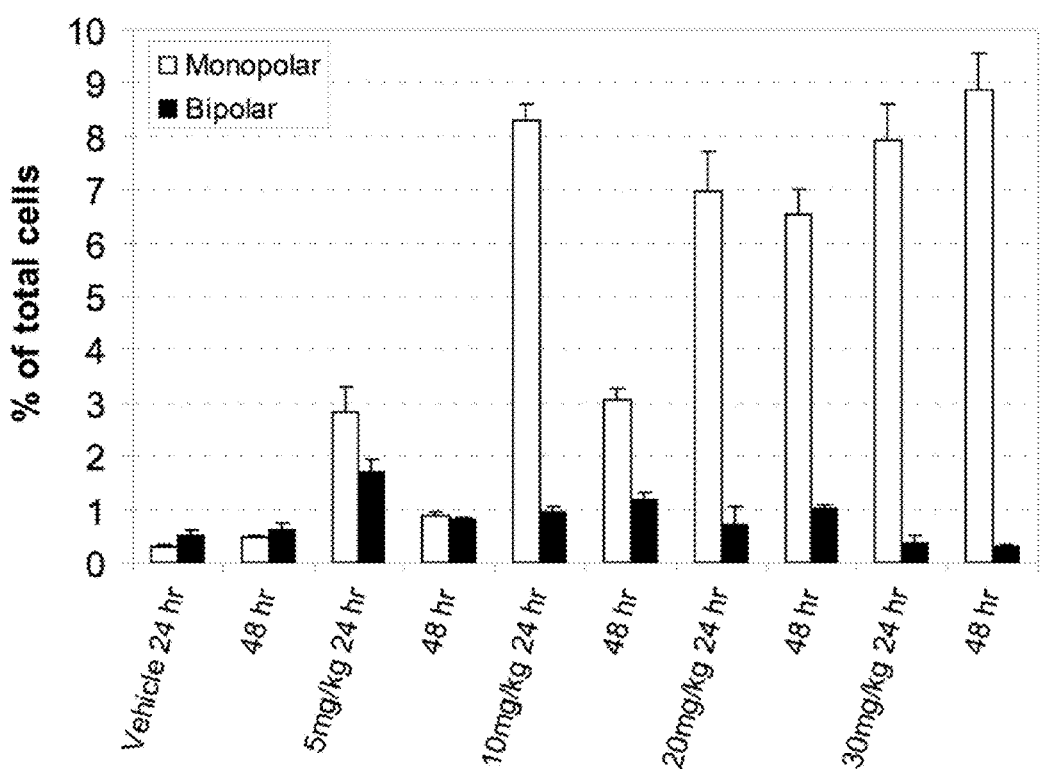
FIG. 8 shows the percentage of cells with monopolar spindles and bipolar spindles in subcutaneous HT-29 xenografts in nude mice at 24 hours and 48 hours for various dose amounts.
Figure 9:
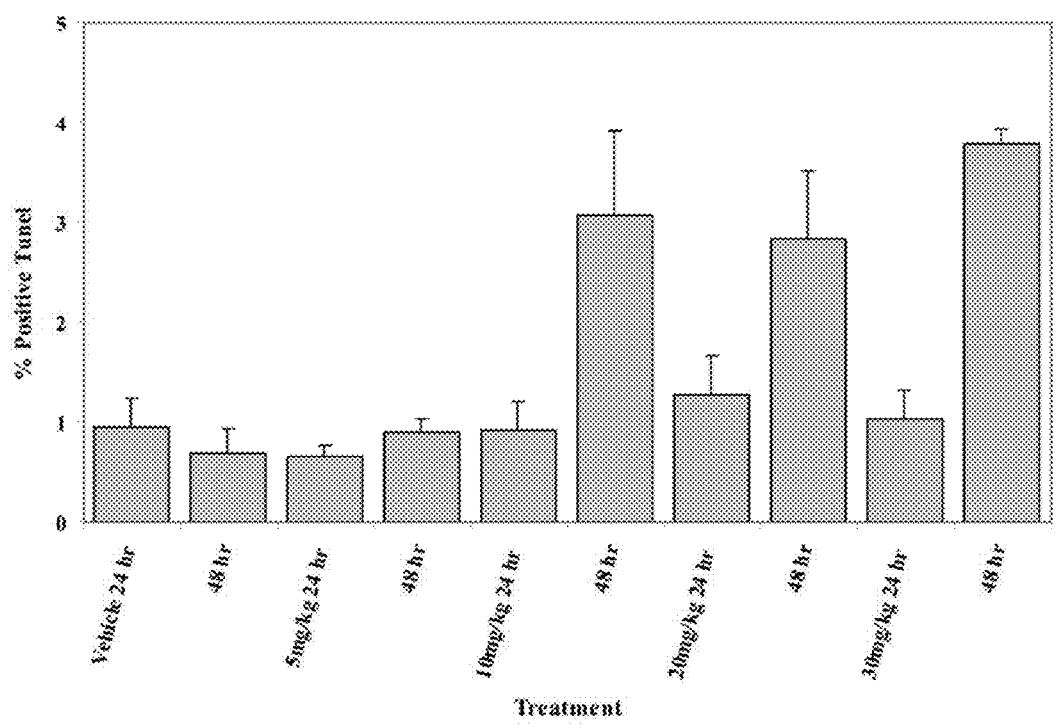
FIG. 9 shows the percentage of apoptotic cells in subcutaneous HT-29 xenografts in nude mice at 24 hours and 48 hours for various dose amounts.

Female nude mice were implanted subcutaneously with $3\times10^6$ HT-29 cells in 100 μL PBS. Fourteen days later, tumors were measured and mice randomized into groups of three with average tumor volume in each group of approximately 300 mm$^3$. Dosing was vehicle alone, and Compound 4 at 5, 10, 20 and 30 mg/kg. All samples were collected 24 and 48 hours after dosing. All other methods were as described for Example 4. The results are shown in FIGS. 8 and 9.

Example 7

Tumor Growth Inhibition on Different Dosing Schedules (HT-29)

Figure 10:
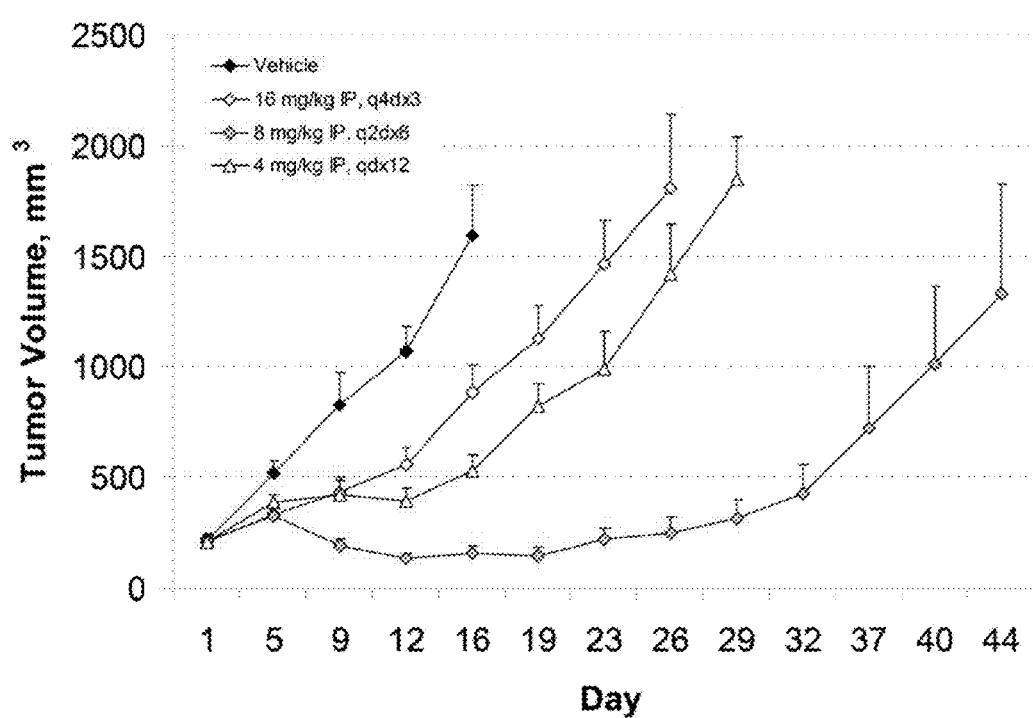
FIG. 10 shows a tumor growth inhibition ("TGI") experiment in nude mice with subcutaneous HT-29 xenografts.
Figure 11:
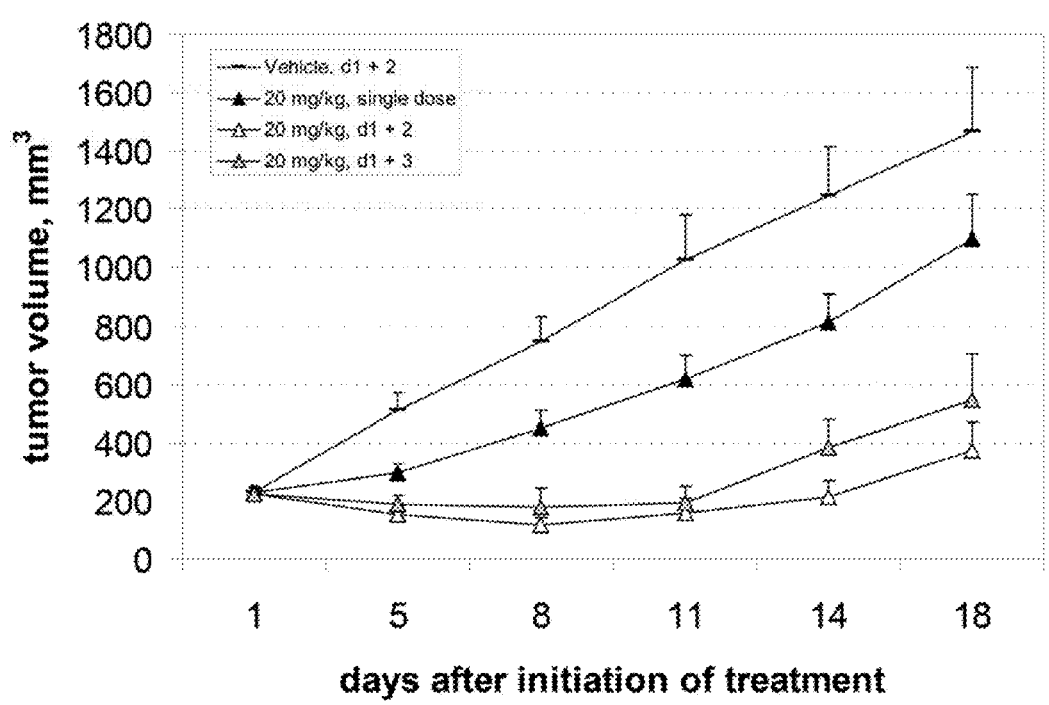
FIG. 11 shows a TGI experiment in nude mice with subcutaneous HT-29 xenografts.
Figure 12:
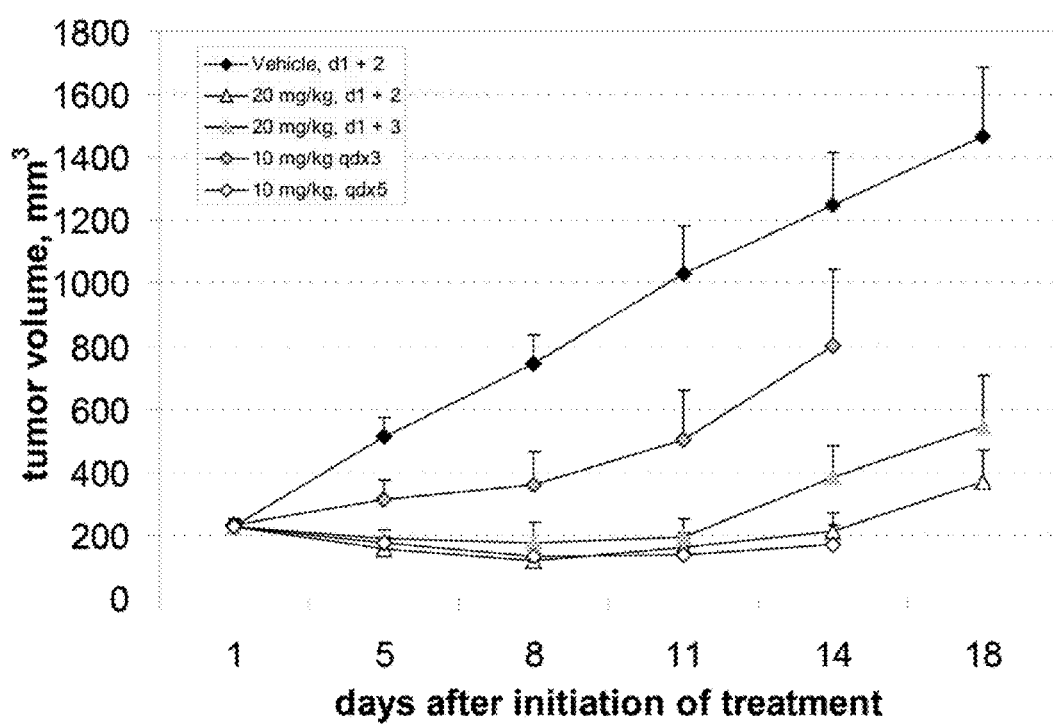
FIG. 12 shows a TGI experiment in nude mice with subcutaneous HT-29 xenografts.
Figure 13:
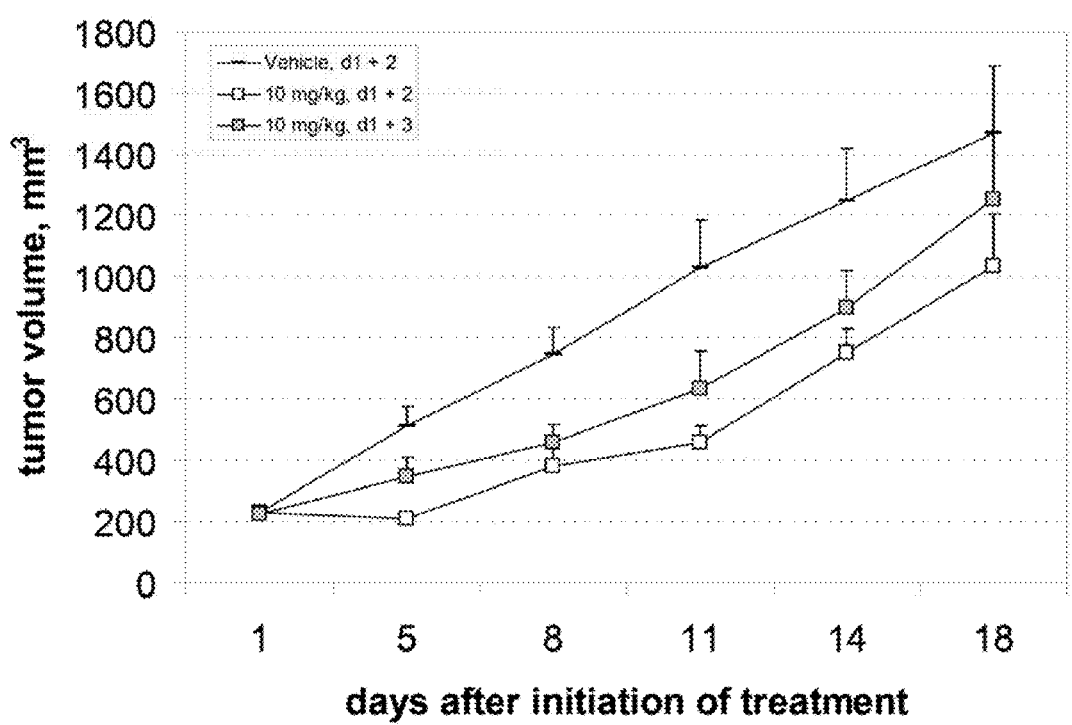
FIG. 13 shows a TGI experiment in nude mice with subcutaneous HT-29 xenografts.
Figure 14:
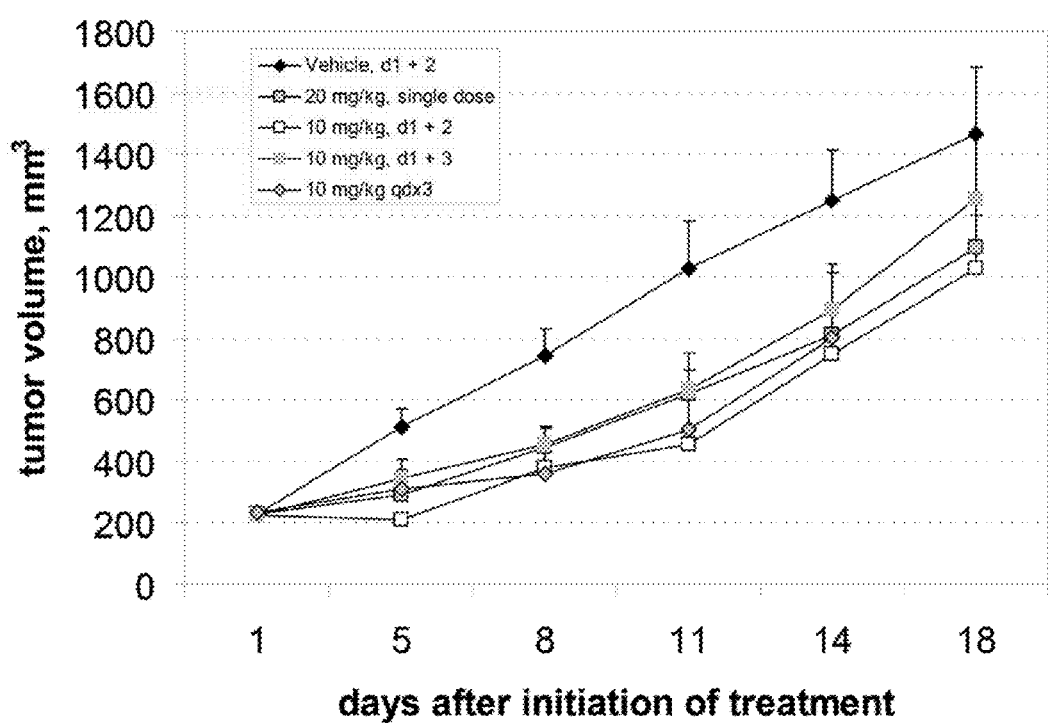
FIG. 14 shows a TGI experiment in nude mice with subcutaneous HT-29 xenografts.
Figure 15:
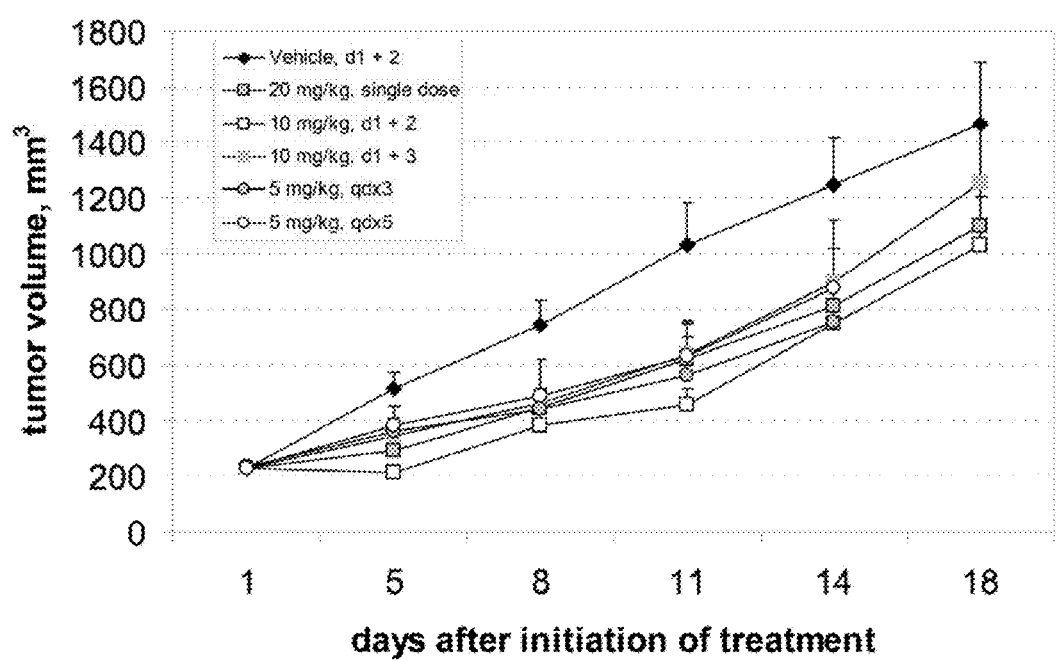
FIG. 15 shows a TGI experiment in nude mice with subcutaneous HT-29 xenografts.

Female nude mice were implanted subcutaneously with $4\times10^6$ HT-29 cells in 100 μL PBS. Thirteen days later, tumors were measured and mice randomized into groups of eight with average tumor volume in each group of approximately 210 mm$^3$. Compound 4 was dissolved in normal saline immediately prior to dosing, and administered IP at a volume of 10 mL/kg for 12 days at doses of 4 mg/kg every day, 8 mg/kg every other day, and 16 mg/kg every fourth day. Animal weights and tumor volumes were measured (using electronic calipers) twice a week. Tumor volume was calculated using the formula: volume=(width$^2$×length)/2. The results are shown in FIG. 10.

Example 8

Tumor Growth Inhibition on Different Dosing Schedules (HT-29)

Female nude mice were implanted subcutaneously with $5\times10^6$ HT-29 cells in 100 μL PBS. Eleven to fourteen days later, tumors were measured and mice randomized into groups of seven with average tumor volume in each group of approximately 230 mm$^3$. Compound 4 was dissolved in normal saline immediately prior to dosing, and administered IP at a volume of 10 mL/kg. Dosing was vehicle alone on day 1 and day 2; and Compound 4 at 20 mg/kg on day 1; 20 mg/kg on days 1 and 2; 20 mg/kg on days 1 and 3; 5 mg/kg on days 1, 2 and 3; 10 mg/kg on days 1, 2 and 3; 10 mg/kg on days 1, 2, 3, 4 and 5; 10 mg/kg on days 1 and 2; and 10 mg/kg on days 1 and 3. Animal weights and tumor volumes were measured (using electronic calipers) twice a week. Tumor volume was calculated using the formula: volume=(width$^2$×length)/2. Dosing at 10 mg/kg on days 1, 2, 3, 4 and 5 was not tolerated (greater than 20% weight loss and/or death in some of the mice). The results are shown in FIGS. 11-15.

Example 9

Tumor Growth Inhibition on Different Dosing Schedules (RPMI 8226)

Female SCID-beige mice were implanted subcutaneously with $1\times10^7$ RPMI 8226 cells in 100 μL PBS with 50% Matrigel. Twenty-five days later, tumors were measured and mice randomized into groups of seven with average tumor volume in each group of approximately 225 mm$^3$. Compound 4 was dissolved in normal saline immediately prior to dosing, and administered IP at a volume of 10 mL/kg. Dosing was vehicle alone on day 1; and Compound 4 at 20 mg/kg on day 1; 10 mg/kg on days 1 and 2; 10 mg/kg on days 1 and 3; and 20 mg/kg on days 1, 5 and 9. Animal weights and tumor volumes were measured (using electronic calipers) twice a week. Tumor volume was calculated using the formula volume=(width$^2$×length)/2. The results are shown in FIG. 16.

Example 10

Duration of Monopolar Spindles, Bipolar Spindles and Magnitude of Apoptosis (RPMI 8226)

Figure 17:
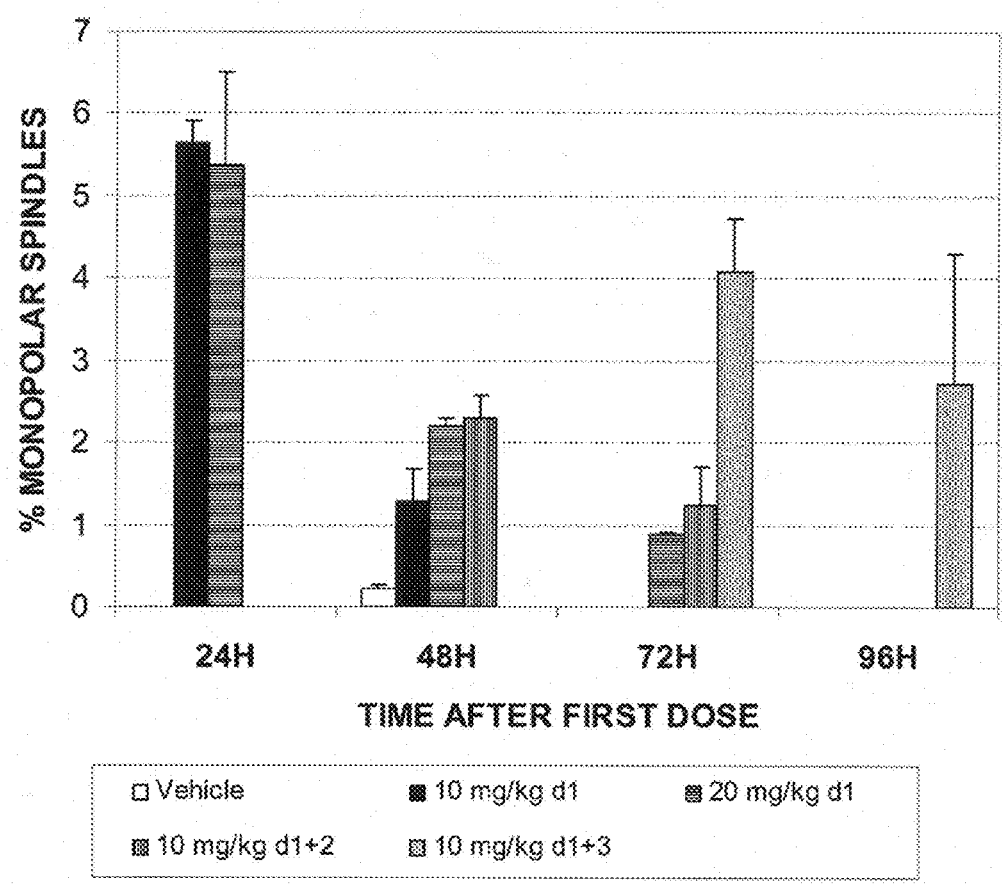
FIG. 17 shows the percentage of monopolar spindles in subcutaneous RPMI8226 xenografts in SCID-beige mice at various time points for different dosing schedules.
Figure 18:
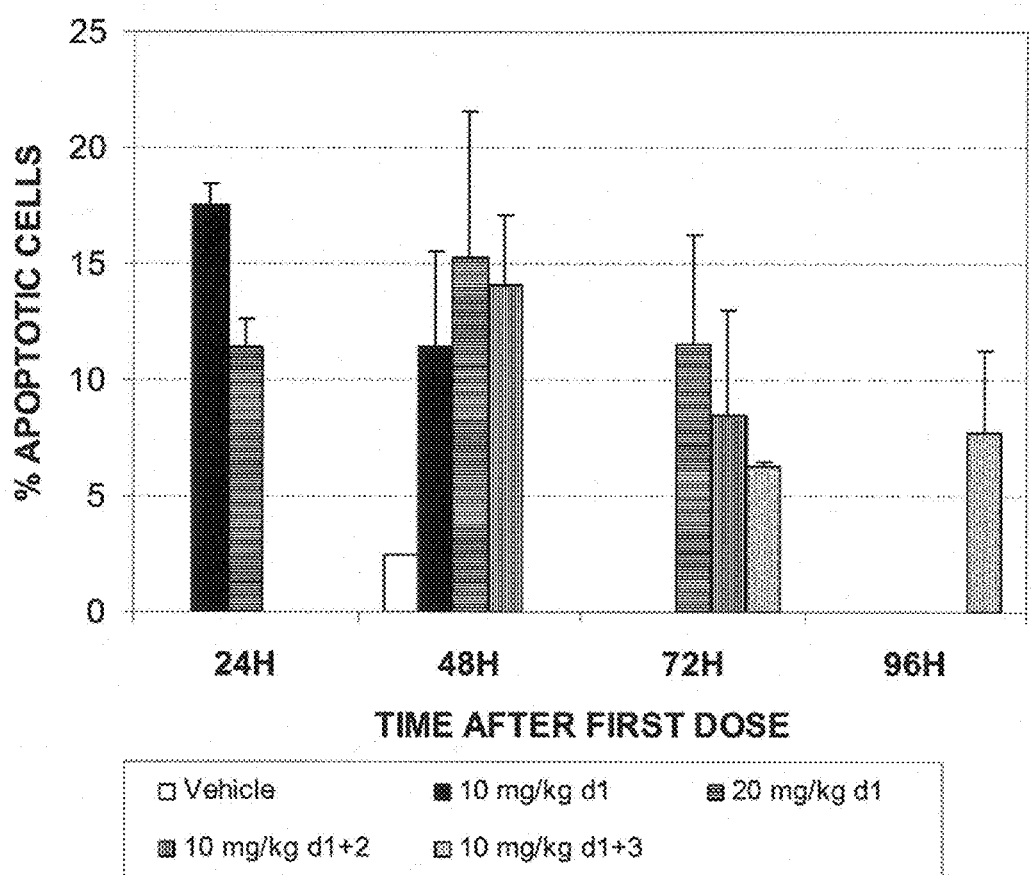
FIG. 18 shows the percentage of apoptotic cells in subcutaneous RPMI 8226 xenografts in SCID-beige mice at various time points after for different dosing schedules.
Figure 19:
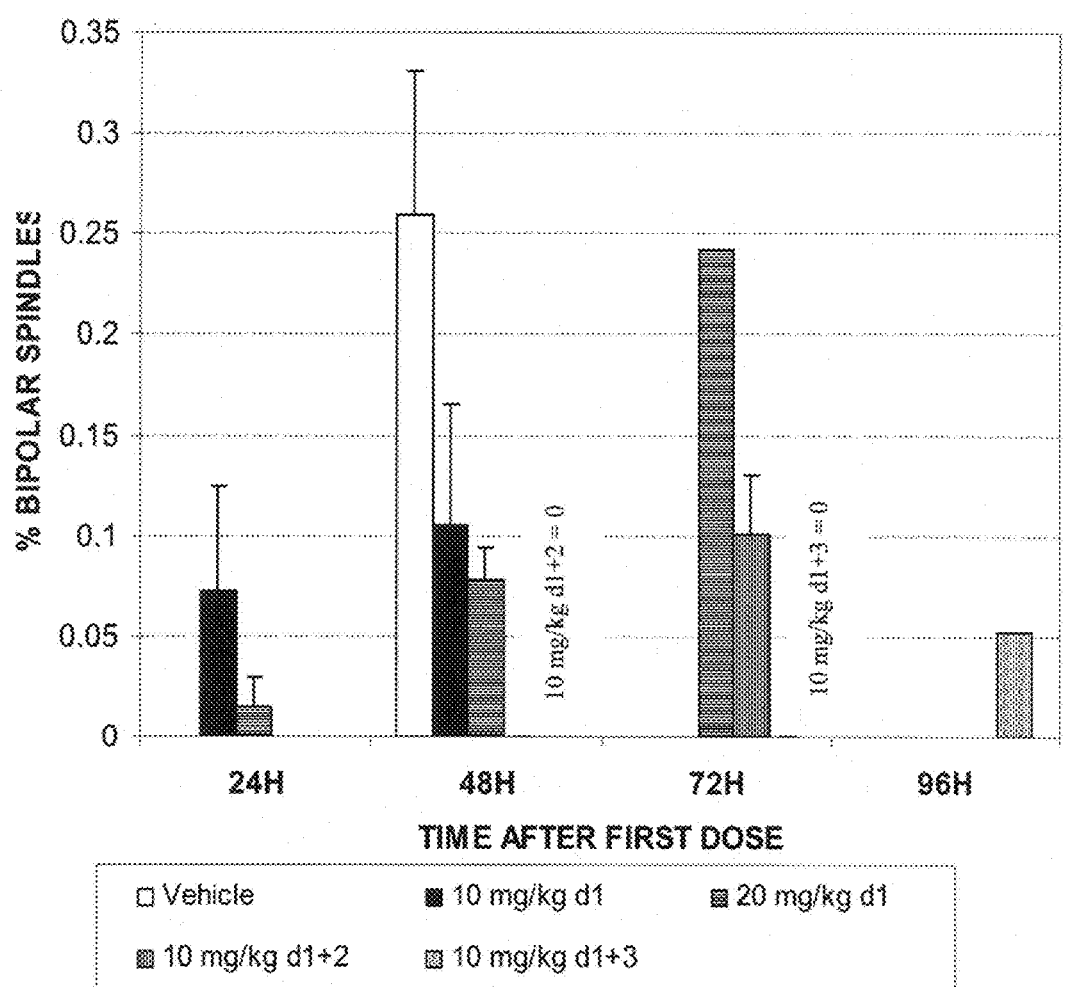
FIG. 19 shows the percentage of bipolar spindles in subcutaneous RPMI 8226 xenografts in SCID-beige mice at various time points for different dosing schedules.

Female SCID-beige mice were implanted subcutaneously with $1 \times 10^7$ RPMI 8226 cells in 100 μL PBS with 50% Matrigel. Thirty-one days later, tumors were measured and mice randomized into groups of three with average tumor volume in each group of approximately 210 mm$^3$. Compound 4 was dissolved in normal saline immediately before dosing. Dose volume was 10 mL/kg. Dosing was vehicle alone on day 1; and Compound 4 at 10 mg/kg on day 1; 20 mg/kg on day 1; 10 mg/kg on days 1 and 2; and 10 mg/kg on days 1 and 3. At various times after dosing (24, 48, 72 and 96 hours), mice were euthanized by $CO_2$ inhalation, and tumors were harvested and immediately placed in formalin. The vehicle control group samples were collected 48 hours after dosing. The 10 mg/kg on day 1 samples were collected 24 and 48 hours after dosing. The 20 mg/kg on day 1 samples were collected 24, 48 and 72 hours after dosing. The 10 mg/kg on days 1 and 2 samples were collected 48 and 72 hours after the first dose. The 10 mg/kg on days 1 and 3 samples were collected 72 and 96 hours after the first dose. Paraffin blocks of tumor tissue were prepared by standard procedures. Visualization of monopolar spindles was carried out by staining cut sections with mouse anti-human alpha tubulin primary antibody (clone B-7, Santa Cruz Biotechnology), followed by goat anti-mouse secondary antibody conjugated to Alexafluor 488 (Invitrogen). Nuclei were stained with Hoechst 33342 for cell counting. Spindle structures were manually counted in three 40× areas of each sample, using a fluorescent microscope. Apoptosis was quantitated by manual counting of TUNEL positive cells, also in three 40× areas of each sample (TUNEL staining using the In Situ Cell Death Detection Kit, AP from Roche). The results are shown in FIGS. 17, 18 and 19.

Example 11

Determination of MTD in a Phase 1 Study

A total of 13 patients with various solid tumors and with a median age of 66 years (range 40-79 years old) were enrolled in a human phase 1 clinical trial (see "Phase I Safety and Pharmacokinetic Study of ARRY-520 in Solid Tumors." http://clinicaltrials.gov/ct2/show/NCT00462358, herein incorporated by reference). The solid tumors treated were breast cancer (2), colorectal cancer (2), non-small cell lung cancer (2), pancreatic cancer (2), bladder cancer, salivary gland cancer (adenoid cystic), esophageal cancer, mesothelioma cancer, and a mixed small cell lung cancer/non-small cell lung cancer. Compound 4 was provided for administration as a lyophilized powder contained in a Type 1 clear glass vial for IV use. The dose levels administered were 1.25 and 1.6 mg/m$^2$/day of Compound 4 on Days 1 and 2 every two weeks. The MTD was determined to be 1.25 mg/m$^2$/day (cumulative dose per cycle of 2.5 mg/m$^2$), with DLTs of Grade 3 hyponatremia, anorexia, AST increase and febrile neutropenia.

See also, "A Phase 1/2 Study of ARRY-520 in Patients With Relapsed or Refractory Multiple Myeloma." http://clinicaltrials.gov/ct2/show/NCT00821249, herein incorporated by reference.

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed:

1. A method of treating cancer by administering to a patient in need thereof two doses of (S)-2-(3-aminopropyl)-5-(2,5-difluorophenyl)-N-methoxy-N-methyl-2-phenyl-1,3,4-thiadiazole-3(2H)-carboxamide, wherein each dose is 1.25 mg/m$^2$/day in a 14 day dosing cycle, wherein the first dose is administered on day one of the dosing cycle and the second dose is administered on day two of the dosing cycle, and the cancer is a hematological tumor.

2. The method of claim 1, wherein the cancer is multiple myeloma or acute myeloid myeloma.

3. The method of claim 2, wherein the cancer is multiple myeloma.

* * * * *